(12) United States Patent
Watahiki et al.

(10) Patent No.: US 8,546,609 B2
(45) Date of Patent: Oct. 1, 2013

(54) IONIC LIQUID CONTAINING ALLYLSULFONATE ANION

(75) Inventors: Tsutomu Watahiki, Kawagoe (JP);
Kuniaki Okamoto, Kawagoe (JP);
Motoshige Sumino, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 13/393,144

(22) PCT Filed: Aug. 30, 2010

(86) PCT No.: PCT/JP2010/064666
§ 371 (c)(1),
(2), (4) Date: Feb. 28, 2012

(87) PCT Pub. No.: WO2011/024988
PCT Pub. Date: Mar. 3, 2011

(65) Prior Publication Data
US 2012/0157680 A1    Jun. 21, 2012

(30) Foreign Application Priority Data
Aug. 31, 2009 (JP) ................................. 2009-200610

(51) Int. Cl.
*C07C 313/00* (2006.01)
(52) U.S. Cl.
USPC ........................................................ 562/114
(58) Field of Classification Search
USPC ........................................................ 562/114
See application file for complete search history.

(56) References Cited

U.S. PATENT DOCUMENTS

| 5,106,912 | A | 4/1992 | Yamamoto et al. |
| 5,143,675 | A | 9/1992 | Yamamoto et al. |
| 5,175,059 | A | 12/1992 | Yamamoto et al. |
| 2008/0045723 | A1 | 2/2008 | Cassol et al. |

FOREIGN PATENT DOCUMENTS

| EP | 0 474 896 A1 | 3/1992 |
| JP | 56-142528 A | 11/1981 |
| JP | 02-225536 A | 9/1990 |
| JP | 03-028270 A | 2/1991 |
| JP | 2001-172614 A | 6/2001 |
| JP | 2001-283635 A | 10/2001 |
| JP | 2004-292350 A | 10/2004 |
| JP | 2004-331521 A | 11/2004 |
| JP | 2005-232019 A | 9/2005 |
| JP | 2005-325052 A | 11/2005 |
| JP | 2007-153856 A | 6/2007 |

OTHER PUBLICATIONS

Cassol et al. Adv. Synth. Catal. 2006, 348, 243-248.*
Kosilkin et al. Chem. Mater. 2010, 22, 4838-4840.*
Blesic et al., *Physical Chemistry Chemical Physics*, 11: 8939-8948 (2009).
Cassol et al., *Adv. Synth. Catal.*, 348: 243-248 (2006).
Nobuoka et al., *J. Org. Chem.*, 70: 10106-10108 (2005).
Wuts et al., *Synthesis*, 11: 1593-1595 (1998).
Japanese Patent Office, International Search Report in International Patent Application No. PCT/JP2010/064666 (Oct. 5, 2010), English translation.

* cited by examiner

*Primary Examiner* — Nizal Chandrakumar
(74) *Attorney, Agent, or Firm* — Leydig, Voit & Mayer, Ltd.

(57) ABSTRACT

Problem:
Providing a novel ionic liquid, which is low-cost, environment-friendly, and has low viscosity and melting point.
Means for Solving the Problem:
The present invention is the invention of the ionic liquid represented by the general formula [1]:

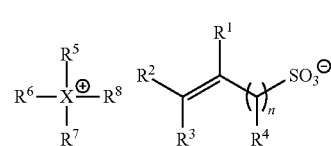

[1]

{wherein, $R^1$ to $R^3$ and n pieces of $R^4$ each independently represent hydrogen atom or alkyl group having 1 to 4 carbon atoms, $R^5$ to $R^7$ each independently represent alkyl group, aralkyl group, or aryl group, $R^8$ represents alkyl group, aralkyl group, aryl group, or the one represented by the general formula [2]:

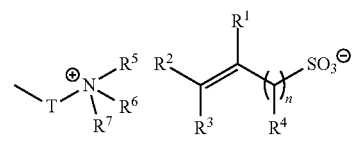

[2]

(wherein T represents alkylene chain having 1 to 8 carbon atoms, n represents 1 or 2, and $R^1$ to $R^7$ are the same as the above-described), X represents nitrogen atom or phosphorus atom, n represents 1 or 2. When n is 1, $R^3$ and $R^4$ are bound and may form cyclohexene ring together with the adjacent carbon atoms. In addition, when X is nitrogen atom, $R^5$ to $R^7$ or $R^5$ to $R^6$ may form hetero ring with nitrogen atom binding thereto}.

6 Claims, No Drawings

IONIC LIQUID CONTAINING ALLYLSULFONATE ANION

TECHNICAL FIELD

The present invention relates to a novel ionic liquid, which is unexpensive in production cost, environment-friendly, and has low viscosity and melting point.

BACKGROUND ART

The ionic liquid can be said as ambient temperature molten salt, and is composed of cation component and anion component, for example, has properties of high heat-resistance, wide temperature range in a liquid state, non-volatility, high ionic conductivity, high solubility to polymer or salt, and the like.

The ionic liquid having such properties is expected to have application to various fields, for example, uses such as solvent for chemical reaction, electrolyte for electrochemical device, antistatic agent, lubricant, are expected.

A number of ionic liquids having a fluorine atom as anion component (for example, $N(CF_3SO_2)_2^-$, $CF_3SO_3^-$, $BF_4^-$, $PF_6^-$, and the like) are reported, but these ionic liquids having a fluorine atom have problems such as adverse effect for ecology due to generation of halogen compound, for example, by thermal decomposition, corrosion of equipment, high production cost due to high content of fluorine.

On the other hand, as the ionic liquid having non-halogenic anion, for example, the ionic liquid using organic acid anion such as anion derived from camphor sulfonic acid (non-patent literature 1), anion derived from sulfosuccinic acid (patent literature 1), for example, the ionic liquid having anion other than organic acid anion such as cyanomethide anion (non-patent literature 2), dicyanamide anion (non-patent literature 3), tetrazole anion(non-patent literature 4) have been developed.

However, the ionic liquid having these organic acid anion has the problems that viscosity is relatively high even though melting temperature shows low, and the like, in addition, the ionic liquid having non-halogenic anion other than organic acid anion has the problems that many synthetic processes are needed, therefore, operation is complicated, expensive raw materials such as silver salt are needed for the necessary salt exchanging, furthermore, uses thereof are limited because metal(silver) ion is contaminated to the ionic liquid obtained by salt exchanging, and the like.

In addition, as ionic liquid having lower alkane sulfonate even in organic acid anion, for example, 1-butyl-3-methylimidazolium methanesulfonate, 1,3-dimethylimidazolium methanesulfonate, 1-butyl-3-methylimidazolium 2-butanesulfonate, and the like have been developed (patent literature 5, non-patent literature 2, non-patent literature 3). However, they have also problems of high melting point.

Furthermore, ionic liquid obtained by disappearing polymerizability of polymeric functional group of salt monomer consisting of cation having polymeric functional group and anion having polymeric functional group have been developed (patent literature 6).

However, this ionic liquid is the one obtained by finally disappearing polymerizability of polymeric functional group, therefore, no polymeric functional group exists in cation or anion. Also, ionic liquid containing allylsulfonate anion as anion, is not specifically disclosed.

Under such circumstances, novel ionic liquid, which has low production cost, and is environment-friendly, and has low melting point and viscosity, is desired to be developed.

PRIOR ART LITERATURES

Patent Literatures
 Patent Literature-1: JP-A-2005-232019:
 Patent Literature-2: JP-A-2004-292350;
 Patent Literature-3: JP-A-2005-325052;
 Patent Literature-4: JP-A-2004-331521;
 Patent Literature-5: US 2008/45723;
 Patent Literature-6: JP-A-2007-153856;
Non-Patent Literatures
 Non-Patent Literature-1: J. Org. Chem., 2005, 70, 10106;
 Non-Patent Literature-2: Adv. Synth. Catal., 2006, 348, 243-248;
 Non-Patent Literature-3: Phys. Chem. Chem. Phys., 2009, 11, 8939-8948;

DISCLOSURE OF INVENTION

Problems to be Solved by the Invention

The present invention has been carried out under the above-described circumstance, therefore, it is the object to provide a novel ionic liquid, which has low production cost, and is environment-friendly, and has low melting point and viscosity.

Means for Solving the Problem

The present invention is the invention of ionic liquid represented by the general formula [1]:

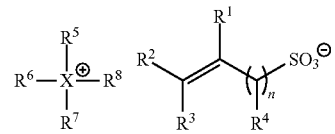

[1]

{wherein $R^1$ to $R^3$ and n pieces of $R^4$ each independently represent a hydrogen atom, or an alkyl group having 1 to 4 carbon atoms, and $R^5$ to $R^7$ each independently represent an alkyl group which may have a hydroxyl group or an alkoxy group as substituent, an aralkyl group or an aryl group, and $R^8$ represents an alkyl group which may have a hydroxy group or an alkoxy group as substituent, an aralkyl group, an aryl group, or the one represented by the general formula [2]

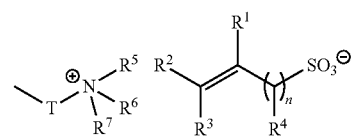

[2]

(wherein T represents alkylene chain having 1 to 8 carbon atoms, n represents 1 or 2, and $R^1$ to $R^7$ are the same as the above-describe), X represents a nitrogen atom or a phosphorus atom, n represents 1 or 2. When n is 1, $R^3$ and $R^4$ may be bound together with the adjacent carbon atoms to form cyclohexene ring. In addition, when X is a nitrogen atom, $R^5$ to $R^7$, or $R^5$ to $R^6$ may form hetero ring with a nitrogen atom binding thereto. When $R^8$ is represented by the general formula [2], X is a nitrogen atom}.

Effect of the Invention

The conventional ionic liquid has, for example, the problems that the ionic liquid containing halogenic anion shows corrosive property due to generation of halogen compound by thermal decomposition, therefore, leading the adverse effect to environment and the like, for example, the problems that ionic liquid having organic acid anion derived from alkane sulfonic acid and the like has high melting point, and the like, in addition, the problems that the ionic liquid having anion derived from camphor sulfonic acid even in organic acid anion shows low melting point, however, viscosity is high, and the like.

On the other hand, ionic liquid of the present invention has no these problems, and has the effect of low melting point and viscosity even though it is non-halogenic anion. For this reason, they can be used for reaction solvent, extraction solvent, lubricant, and the like.

In addition, since the ionic liquid of the present invention is expected to have a good ionic conductivity, it is suitable for electrolyte for electrochemical device such as various types of storage device, solar cell, fuel cell, or additives thereof, and conductive material for antistatic agent, and the like.

BEST MODE FOR CARING OUT THE INVENTION

Among the ionic liquid represented by the general formula [1], when $R^8$ is a alkyl group which may have a hydroxy group or an alkoxy group as substituent, an aralkyl group or an aryl group, specific example thereof includes, for example, the one represented by the general formula [3]

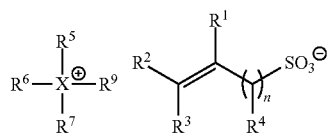

[3]

(wherein, $R^1$ to $R^3$ and n pieces of $R^4$ each independently represent a hydrogen atom or an alkyl group having 1 to 4 carbon atoms, and $R^5$ to $R^7$ each independently represent an alkyl group which may have a hydroxyl group or an alkoxy group as substituent, an aralkyl group or an aryl group, $R^9$ represents a alkyl group which may have a hydroxy group or an alkoxy group as substituent, an aralkyl group or an aryl group, X represents a nitrogen atom or a phosphorus atom, and n represents 1 or 2. When n is 1, $R^3$ and $R^4$ may be bound to form a cyclohexene ring together with the adjacent carbon atoms. In addition, when X is a nitrogen atom, $R^5$ to $R^7$, or $R^5$ to $R^6$ may form hetero ring with a nitrogen atom bound thereto), when $R^8$ is the one represented by the general formula [2], specific example thereof includes, for example, the one represented by the general formula [4]:

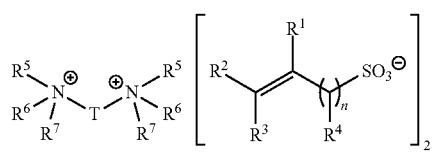

[4]

(wherein $R^1$ to $R^3$, n pieces of $R^4$, 2 pieces of $R^5$ to $R^7$, T and n are the same as the above-described).

In the general formula [1] to [4], an alkyl group having 1 to 4 carbon atoms represented by $R^1$ to $R^3$, and n pieces of $R^4$ may be any of a straight chain, a branched, or a cyclic group, and it includes usually the one having 1 to 4 carbon atoms, preferably 1 to 2, more preferably 1, and specifically, includes, for example, a methyl group, an ethyl group, a n-propyl group, an isopropyl group, a n-butyl group, an isobutyl group, a sec-butyl group, a tert-butyl group and like, among them, a methyl group is preferable.

n is 1 or 2, preferably 1.

Alkyl group of alkyl group which may have a hydroxyl group or an alkoxy group as substituent represented by $R^5$ to $R^9$ may be any of a straight chain, a branched, or a cyclic group, and it includes usually the one having 1 to 8 carbon atoms, preferably 1 to 4 carbon atoms, and specifically, includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a cyclopropyl group, a cyclobutyl group, a cyclopentyl group, a cyclohexyl group, a cycloheptyl group, a cyclooctyl group, and the like.

Alkoxy group exemplified as substituent of said alkyl group represented by $R^5$ to $R^9$ may be any of a straight chain, a branched, or a cyclic group, includes usually the one having 1 to 8 carbon atoms, preferably 1 to 4, and specifically, includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a 1-methylpentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a cyclopropoxy group, a cyclobutoxy group, a cyclopentyloxy group, a cyclohexyloxy group, a cycloheptyloxy group, a cyclooctyloxy group, and the like.

Preferable specific example of alkyl group having hydroxyl group as substituent represented by $R^5$ to $R^9$ includes, for example, a hydroxyethyl group, a hydroxypropyl group, a hydroxybutyl group, a hydroxypentyl group, a hydroxyhexyl group, a hydroxyheptyl group, a hydroxyoctyl group, and the like.

Preferable specific example of alkyl group having alkoxy group represented by $R^5$ to $R^9$ as substituent includes, for example, a methoxyethyl group, an ethoxyethyl group, a propoxyethyl group, an isopropoxyethyl group, a n-butoxyethyl group, an isobutoxyethyl group, a sec-butoxyethyl group, a tert-butoxyethyl group, a n-pentyloxyethyl group, an isopentyloxyethyl group, a sec-pentyloxyethyl group, a tert-pentyloxyethyl group, a neopentyloxyethyl group, a cyclopentyloxyethyl group, a n-hexyloxyethyl group, an isohexyloxyethyl group, a sec-hexyloxyethyl group, a tert-hexyloxyethyl group, a neohexyloxyethyl group, a cyclohexyloxyethyl group, a methoxypropyl group, an ethoxypropyl group, a propoxypropyl group, an isopropoxypropyl group, a n-butoxypropyl group, an isobutoxypropyl group, a sec-butoxypropyl group, a tert-butoxypropyl group, a n-pentyloxypropyl group, an isopentyloxypropyl group, a sec-pentyloxypropyl group, a tert-pentyloxypropyl group, a neopentyloxypropyl group, a cyclopentyloxypropyl group, a n-hexyloxypropyl group, an isohexyloxypropyl group, a sec-hexyloxypropyl group, a tert-hexyloxypropyl group, a neohexyloxypropyl group, a cyclohexyloxypropyl group, a methoxybutyl group, an ethoxybutyl group, a propoxybutyl group, an isopropoxybutyl group, a n-butoxybutyl group, an isobutoxybutyl group, a sec-butoxybutyl group, a tert-butoxybutyl group, a n-pentyloxybutyl group, an isopentyloxybutyl group, a sec-pentyloxybutyl group, a tert-pentyloxybutyl group, a neopentyloxybutyl group, a cyclopentyloxybutyl group, a n-hexyloxybutyl group, an isohexyloxybutyl group, a sec-hexyloxybutyl group, a tert-hexyloxybutyl group, a neohexyloxybutyl group, a cyclohexyloxybutyl group, and the like.

Aralkyl group represented by $R^5$ to $R^9$ includes usually the one having 7 to 9 carbon atoms, and specifically, includes, for example, a benzyl group, a phenethyl group, a phenylpropyl group, and the like.

Hetero cyclic group formed by $R^5$ to $R^7$, or $R^5$ to $R^6$ and a nitrogen atom bound thereto is, for example, 5 membered ring or 6 membered ring, and may contain 1 to 2 hetero atoms(for example, a nitrogen atom, an oxygen atom, a sulfur atom, and the like) other than one nitrogen atom, and specifically, includes, for example, imidazoline ring, pyrazoline ring, piperidine ring, piperazine ring, morpholine ring, thiazoline ring, pyridine ring, pyrazine ring, pyrimidine ring, pyridazine ring, imidazole ring, pyrazole ring, oxazole ring, thiazole ring, pyrrolidine ring, quinoline ring, isoquinoline ring, quinoxaline ring, indoline ring, isoindoline ring, and the like.

Said hetero ring may further have, for example, an alkyl group, an aralkyl group, and the like as substituent, preferable specific example of hetero compound having such substituent includes the one represented by the general formula [5] to [10]:

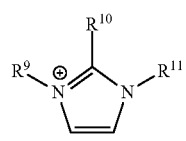

[5]

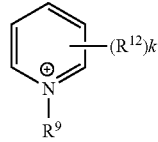

[6]

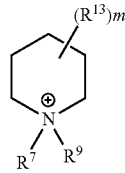

[7]

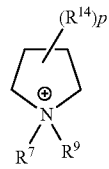

[8]

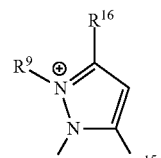

[9]

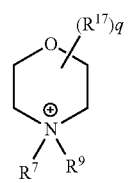

[10]

(wherein $R^{10}$ to $R^{11}$ and $R^{15}$ to $R^{17}$ each independently represent a hydrogen atom, an alkyl group or an aralkyl group, and $R^{12}$ to $R^{14}$ each independently represents a hydrogen atom, an alkyl group, an aralkyl group or an alkoxy group, and k represents an integer of 0 to 5, m represents an integer of 0 to 10, p and q represent integers of 0 to 8, $R^5$ to $R^7$ and $R^9$ are the same as the above-described).

In the general formula [5] to [10], alkyl group represented by $R^{10}$ to $R^{17}$ may be any of a straight chain, a branched, or a cyclic group, it includes usually the one having 1 to 20 carbon atoms, preferably 1 to 18, more preferably 6 to 18, and specifically, includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, an sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a n-nonadecyl group, an isononadecyl group, a sec-nonadecyl group, a tert-nonadecyl group, a neononadecyl group, a n-icosyl group, an isoicosyl group, a sec-icosyl group, a tert-icosyl group, a neoicosyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, and the like.

Aralkyl group represented by $R^{10}$ to $R^{17}$ includes usually the one having 7 to 15 carbon atoms, and specifically, it includes, for example, a benzyl group, a phenethyl group, a phenylpropyl group, a naphthylmethyl group, and the like.

Alkoxy group represented by $R^{12}$ to $R^{14}$ may be any of a straight chain, a branched, or a cyclic group, it includes usually the one having 1 to 8 carbon atoms, preferably 1 to 4, and specifically, includes for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a 1-methylpentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a cyclopropoxy group, a cyclobutoxy group, a cyclopentyloxy group, a cyclohexyloxy group, a cycloheptyloxy group, a cyclooctyloxy group, and the like.

In the general formula [6], k is an integer of usually 0 to 5, preferably 0 to 3, more preferably 0 to 2, furthermore preferably 0 or 1.

In the general formula [7], m is an integer of usually 0 to 10, preferably 0 to 4, more preferably 0 to 2, furthermore preferably 0.

In general formula [8] and [9], p and q are each independently an integer of usually 0 to 8, preferably 0 to 4, more preferably 0 to 2, furthermore preferably 0.

In general formula [2] and [4], alkylene chain having 1 to 8 carbon atoms represented by T may be linear group or branched group, among them, linear group is preferable, it includes the one having usually 1 to 8 carbon atoms, preferably 1 to 4, more preferably 1 to 2, and specifically, includes for example, a methylene group, an ethylene group, a trimethylene group, a tetramethylene group, a pentamethylene group, a hexamethylene group, a heptamethylene group, an octamethylene group, and the like, among them, a methylene group is preferable.

Preferable specific example of cation moiety in the general formula [3] includes, for example, the one represented by the general formula [5] to [10], and the one represented by the following general formula [11] to [12]:

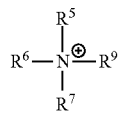

[11]

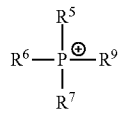

[12]

(wherein $R^5$ to $R^7$ and $R^9$ are the same as the above-described).

In cation moiety represented by the general formula [3], the one represented by the general formula [5] to [8] or [10] to [12] is preferable, particularly the one represented by the general formula [5] to [8] or [10] is more preferable.

Preferable specific example of cation moiety in the general formula [4] includes, for example, the one represented by the general formula [13] to [20] and the like, among them, the one represented by the general formula [13] to [14] is preferable

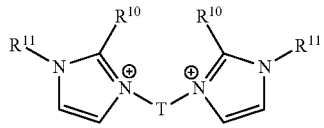

[13]

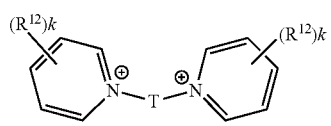

[14]

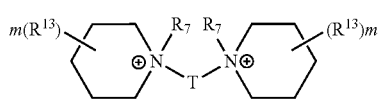

[15]

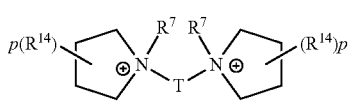

[16]

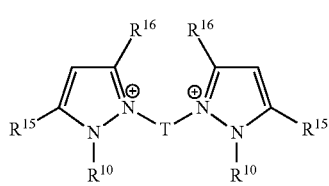

[17]

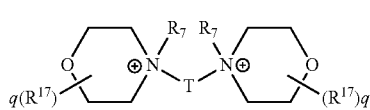

[18]

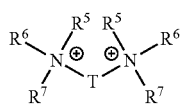

[19]

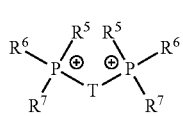

[20]

(wherein $R^5$ to $R^7$, $R^{10}$ to $R^{17}$, T, k, m, p and q are the same as the above-described).

Even in the cation moiety in the general formula [1], cation represented by the general formula [3] is preferable, particularly the one represented by the general formula [5] to [8] or [10] is more preferable.

Preferable specific example of imidazolium cation represented by the general formula [5] includes, for example, 3-methylimidazolium ion, 3-ethylimidazolium ion, 3-butylimidazolium ion, 3-pentylimidazolium ion, 3-hexylimidazolium ion, 3-octylimidazolium ion, 3-decylimidazolium ion, 3-dodecylimidazolium ion, 3-tetradecylimidazolium ion, 3-hexadecylimidazolium ion, 3-octadecylimidazolium ion, 2,3-dimethylimidazolium ion, 2-methyl-3-ethylimidazolium ion, 2-methyl-3-butylimidazolium ion, 2-methyl-3-propylimidazolium ion, 2-methyl-3-hexylimidazolium ion, 2-methyl-3-hexadecylimidazolium ion, 1,3-dimethylimidazolium ion, 1-methyl-3-pentylimidazolium ion, 1-methyl-3-hexylimidazolium ion, 1-methyl-3-octylimidazolium ion, 1-methyl-3-decylimidazolium ion, 1-methyl-3-dodecylimidazolium ion, 1-methyl-3-tetradecylimidazolium ion, 1-methyl-3-hexadecylimidazolium ion, 1-methyl-3-octadecylimidazolium ion, 1,3-diethylimidazolium ion, 1-ethyl-3-methylimidazolium ion, 1-ethyl-2,3-dimethylimidazolium ion, 1-ethyl-3-butylimidazolium ion, 1-ethyl-3- pentylimidazolium ion, 1-ethyl-3-hexylimidazolium ion, 1-ethyl-3-octylimidazolium ion, 1-ethyl-3-decylimidazolium ion, 1-ethyl-3-dodecylimidazolium ion, 1-ethyl-3-tetradecylimidazolium ion, 1-ethyl-3-hexadecylimidazolium ion, 1-ethyl-3-octadecylimidazolium ion, 1-propyl-3-methylimidazolium ion, 1-isopropyl-3-methylimidazolium ion, 1-butyl-3-methylimidazolium ion, 1-butyl-2,3-dimethylimidazolium ion, 1-allyl-3-methylimidazolium ion, 1-allyl-3-ethylimidazolium ion, 1-allyl-3-butylimidazolium ion, 3-benzylimidazolium ion, 3-phenylethylimidazolium ion, 3-phenylpropylimidazolium ion, 1-methyl-3-benzylimidazolium ion, 1-methyl-3-phenylethylimidazolium ion, 1-methyl-3-phenylpropylimidazolium ion, 1,2,3-trimethylimidazolium ion, 1,2-dimethyl-3-ethylimidazolium ion, 1,2-dimethyl-3-butylimidazolium ion, 1,2-dimethyl-3-propylimidazolium ion, 1,2-dimethyl-3-hexylimidazolium ion, 1,2-dimethy-13-hexadecylimidazolium ion, and the like.

Preferable specific example of pyridinium cation represented by the general formula [6] includes, for example, pyridinium ion, 3-methylpyridinium ion, 3-ethylpyridinium ion, 4-methylpyridinium ion, 4-ethylpyridinium ion, 3,4-dimethylpyridinium ion, 3,5-dimethylpyridinium ion, 1-methylpyridinium ion, 1-ethylpyridinium ion, 1-ethyl-4-methoxypyridinium ion, 1-propylpyridinium ion, 1-isopropylpyridinium ion, 1-butylpyridinium ion, 1-allylpyridinium ion, 1-benzylpyridinium ion, 1-phenylethylpyridinium ion, 1-phenylpropylpyridinium ion, 1,3-dimethylpyridinium ion, 1-methyl-3-ethylpyridinium ion, 1,3,5-trimethylpyridinium ion, 1-methyl-3,5-diethylpyridinium ion, 1-(1-butyl)-pyridinium ion, 1-(1-hexyl)-pyridinium ion, 1-(1-octyl)-pyridinium ion, 1-(1-hexyl)-pyridinium ion, 1-(1-octyl)-pyridinium ion, 1-(1-dodecyl)-pyridinium ion, 1-(1-tetradecyl)-pyridinium ion, 1-(1-hexadecyl)-pyridinium ion, 1,2-dimethylpyridinium ion, 1-ethyl-2-methylpyridinium ion, 1-(1-butyl)-2-methylpyridinium ion, 1-(1-hexyl)-2-methylpyridinium ion, 1-(1-octyl)-2-methylpyridinium ion, 1-(1-dodecyl)-2-methylpyridinium ion, 1-(1-tetradecyl)-2-methylpyridinium ion, 1-(1-hexadecyl)-2-methylpyridinium ion, 1-methyl-2-ethylpyridinium ion, 1,2-diethylpyridinium ion, 1-(1-butyl)-2-ethylpyridinium ion, 1-(1-hexyl)-2-ethylpyridinium ion, 1-(1-octyl)-2-ethylpyridinium ion, 1-(1-dodecyl)-2-ethylpyridinium ion, 1-(1-tetradecyl)-2-ethylpyridinium ion, 1-(1-hexadecyl)-2-ethylpyridinium ion, 1,2-dimethyl-5-ethylpyridinium ion, 1,5-diethyl-2-methylpyridinium ion, 1-(1-butyl)-2-methyl-3-ethylpyridinium ion, 1-(1-hexyl)-2-methyl-3-ethylpyridinium ion, 1-(1-octyl)-2-methyl-3-ethylpyridinium ion, 1-(1-dodecyl)-2-methyl-3-ethylpyridinium ion, 1-(1-tetradecyl)-2-methyl-3-ethylpyridinium ion, 1-(1-hexadecyl)-2-methyl-3-ethylpyridinium ion.

Preferable specific example of piperidinium cation represented by the general formula [7] includes, for example, 1,1-dimethylpiperidinium ion, 1-methyl-1-ethylpiperidinium ion, 1,1-diethylpiperidinium ion, 1-methyl-1-propylpiperidinium ion, 1-allyl-1-methylpiperidinium ion, 1-ethyl-1-propylpiperidinium ion, 1,1-dipropylpiperidinium ion, 1-methyl-1-butylpiperidinium ion, 1-ethyl-1-butylpiperidinium ion, 1-propyl-1-butylpiperidinium ion, 1,1-dibutylpiperidinium ion, 1-(hydroxyethyl)-1-methylpiperidinium ion, 1-benzyl-1-methylpiperidinium ion, 1-phenylethyl-1-methylpiperidinium ion, 1-phenylpropyl-1-methylpiperidinium ion, and the like.

Preferable specific example of pyrrolidinium cation represented by the general formula [8] includes, for example, 1,1'-spirobipyrrolidinium, 1,1-dimethylpyrrolidinium ion, 1-methyl-1-ethylpyrrolidinium ion, 1,1-diethylpyrrolidinium ion, 1-methyl-1-propylpyrrolidinium ion, 1-allyl-1-methylpyrrolidinium ion, 1-ethyl-1-propylpyrrolidinium ion, 1,1-dipropylpyrrolidinium ion, 1-methyl-1-butylpyrrolidinium ion, 1-ethyl-1-butylpyrrolidinium, 1-propyl-1-butylpyrrolidinium ion, 1,1-dibutylpyrrolidinium ion, 1-(hydroxyethyl)-1-methylpyrrolidinium ion, 1-benzyl-1-methylpyrrolidinium ion, 1-phenylethyl-1-methylpyrrolidinium ion, 1-phenylpropyl-1-methylpyrrolidinium ion, and the like.

Preferable specific example of pyrazolium cation represented by the general formula [9] includes, for example, 1-ethylpyrazolium ion, 1-propylpyrazolium ion, 1-butylpyrazolium ion, 1-pentylpyrazolium ion, 1-hexylpyrazolium ion, 1-allylpyrazolium ion, 1-butenylpyrazolium ion, 1-methoxymethylpyrazolium ion, 1-methoxyethylpyrazolium ion, 1-ethyl-2,3,5-trimethylpyrazolium ion, 1-propyl-2,3,5-trimethylpyrazolium ion, 1-butyl-2,3,5-trimethylpyrazolium ion, 1-pentyl-2,3,5-trimethylpyrazolium ion, 1-hexyl-2,3,5-trimethylpyrazolium ion, 1-allyl-2,3,5-trimethylpyrazolium, 1-butenyl-2,3,5-trimethylpyrazolium ion, 1-methoxymethyl-2,3,5-trimethylpyrazolium ion, 1-methoxyethyl-2,3,5-trimethylpyrazolium, and the like.

Preferable specific example of morpholinium cation represented by the general formula [10] includes, for example, N,N-dimethylmorpholinium ion, N-ethyl-N-methylmorpholinium ion, N,N-diethylmorpholinium ion, N-propyl-N-methylmorpholinium ion, N,N-dipropylmorpholinium ion, N-butyl-N-methylmorpholinium ion, N,N-dibutylmorpholinium ion, N-ethyl-N-propylmorpholinium ion, N-butyl-N-propylmorpholinium ion, N-butyl-N-ethylmorpholinium ion, N-allyl-N-methylmorpholinium ion, N-allyl-N-ethylmorpholinium ion, and the like.

Preferable specific example of quaternary ammonium cation represented by the general formula [11] includes, for example, tetraalkylammonium ion such as tetraethylammonium ion, tetra-n-propylammonium ion, tetra-n-butylammonium ion, tetra-n-pentylammonium ion, tetra-n-hexylammonium ion, tetra-n-heptylammonium ion, tetra-n-octylammonium ion, trioctylethylammonium ion, triheptylpentylammonium ion, triheptylpropylammonium ion, triheptylmethylammonium ion, trihexylbutylammonium ion, trihexylethylammonium ion, nonyltripentylammonium ion, hexyltripentylammonium ion, tripentylbutylammonium ion, tripentylmethylammonium ion, octyltributylammonium ion, hexyltributylammonium ion, heptyltripropylammonium ion, hexyltripropylammonium ion, tripropylmethylammonium ion, octyltriethylammonium ion, triethylmethylammonium ion, trimethyloctylammonium ion, hexyltrimethylammonium ion, ethyltrimethylammonium ion, octylhexyldipentylammonium ion, octylhexyldipropylammonium ion, octylhexyldimethylammonium ion, octylpentyldibutylammonium ion, octylpentyldipropylammonium ion, octylpentyldimethylammonium ion, octylbutyldipropylammonium ion, octylethyldimethylammonium ion, heptylpentyldimethylammonium ion, hexylpentyldibutylammonium ion, hexylpentyldimethylammonium ion, hexylbutyldimethylammonium ion, pentylbutyldipropylammonium ion; for example, aralkyltrialkylammonium ion such as benzyltrimethylammonium ion, benzyltriethylammonium ion, benzyltripropylammonium ion, benzyltributylammonium ion; for example, allyltrialkylammonium ion such as allyltrimethylammonium ion, allyltriethylammonium ion, allyltripropylammonium ion, allyltributylammonium ion, and the like.

Preferable specific example of phosphonium cation represented by the general formula [12] includes, for example, tetramethylphosphonium ion, tetraethylphosphonium ion, tetrapropylphosphonium ion, tetrabutylphosphonium ion, ethyltrimethylphosphonium ion, triethylmethylphosphonium ion, tricyclohexylmethylphosphonium ion, tributylmethylphosphonium ion, butyltriethylphosphonium ion, and the like.

Preferable specific example of biscation represented by the general formula [13] includes, for example, methylenebis(1,2-dimethylimidazolium) ion, methylenebis(1-butylimidazolium) ion, methylenebis(1-methylimidazolium) ion, ethylenebis(1-butylimidazolium) ion, ethylenebis(1-methylimidazolium) ion, trimethylenebis(1-butylimidazolium) ion, trimethylenebis(1-methylimidazolium) ion, 3-oxapentylbis(1-decylimidazolium) ion, 4-oxahexylbis (1-decylimidazolium) ion, 5-oxanonylbis(1-decylimidazolium) ion, 3,6,9-trioxaundecylbis(1-decylimidazolium) ion, 3,6,9,12-tetraoxatetradecylbis (1-decylimidazolium) ion, 3-thiapentylbis(1-decylimidazolium) ion, 4-thiahexylbis(1-decylimidazolium) ion, 5-thainonylbis(1-decylimidazolium) ion, 3,6,9-trithiaundecylbis(1-decylimidazolium) ion, 3,6,9,12-tetrathiatetradecylbis (1-decylimidazolium) ion, and the like.

Preferable specific example of biscation represented by the general formula [14] includes, for example, methylenebispyridinium ion, methylenebis(3,5-dimethylpyridinium) ion, methylenebis(3-methylpyridinium) ion, ethylenebispyridinium ion, ethylenebis(3-methylpyridinium) ion, trimethylenebispyridinium ion, trimethylenebis(3,5-dimethylpyridinium) ion, trimethylenebis(3-pyridinium) ion, 3-oxapentylbis(3-decylpyridinium) ion, 4-oxahexylbis(3-decylpyridinium) ion, 5-oxanonylbis(3-decylpyridinium) ion, 3,6,9-trioxaundecylbis(3-decylpyridinium) ion, 3,6,9,12-tetraoxatetradecylbis(3-decylpyridinium) ion, 3-thiapentylbis(3-decylpyridinium) ion, 4-thiahexylbis(3-decylpyridinium) ion, 5-thianonylbis(3-decylpyridinium) ion, 3,6,9-trithiaundecylbis(3-decylpyridinium) ion, 3,6,9,12-tetrathiatetradecylbis(3-decylpyridinium) ion, and the like.

Preferable specific example of biscation represented by the general formula [15] includes, for example, methylenebis(1-methylpiperidinium) ion, methylenebis(1-ethylpiperidinium) ion, methylenebis(1-butylpiperidinium) ion, ethylenebis(1-methylpiperidinium) ion, ethylenebis(1-ethylpiperidinium) ion, ethylenebis(1-butylpiperidinium) ion, trimethylenebis(1-methylpiperidinium) ion, trimethylenebis(1-ethylpiperidinium) ion, trimethylenebis(1-butylpiperidinium) ion, and the like.

Preferable specific example of biscation represented by the general formula [16] includes, for example, methylenebis(1-methylpyrrolidinium) ion, methylenebis(1-ethylpyrrolidinium) ion, methylenebis(1-butylpyrrolidinium) ion, ethylenebis(1-methylpyrrolidinium) ion, ethylenebis(1-ethylpyrrolidinium) ion, ethylenebis(1-butylpyrrolidinium) ion, trimethylenebis(1-methylpyrrolidinium) ion, trimethylenebis(1-ethylpyrrolidinium) ion, trimethylenebis(1-butylpyrrolidinium) ion, and the like.

Preferable specific example of biscation represented by the general formula [17] includes, for example, methylenebis(2,3,5-trimethylpyrazolium) ion, methylenebis(2,3,5-trimethylpyrazolium) ion, methylenebis(2,3,5-trimethylpyrazolium) ion, ethylenebis(2,3,5-trimethylpyrazolium) ion, ethylenebis(2,3,5-trimethylpyrazolium) ion, ethylenebis(2,3,5-trimethylpyrazolium) ion, trimethylenebis(2,3,5-trimethylpyrazolium) ion, trimethylenebis(2,3,5-trimethylpyrazolium) ion, trimethylenebis(2,3,5-trimethylpyrazolium) ion, and the like.

Preferable specific example of biscation represented by the general formula [18] includes, for example, methylenebis(N-methylmorpholinium) ion, methylenebis(N-ethylmorpholinium) ion, methylenebis(N-propylmorpholinium) ion, methylenebis(N-butylmorpholinium) ion, ethylenebis(N-methylmorpholinium) ion, ethylenebis(N-ethylmorpholinium) ion, ethylenebis(N-propylmorpholinium) ion, ethylenebis(N-butylmorpholinium) ion, trimethylenebis(N-methylmorpholinium) ion, trimethylenebis(N-ethylmorpholinium) ion, trimethylenebis(N-propylmorpholinium) ion, trimethylenebis(N-butylmorpholinium) ion, and the like.

Preferable specific example of biscation represented by the general formula [19] includes, for example, methylenebis(trimethylammonium) ion, methylenebis(triethylammonium) ion, methylenebis(tripropylammonium) ion, methylenebis(tributylammonium) ion, methylenebis(tripentylammonium) ion, methylenebis(trihexylammonium) ion, methylenebis(trioctylammonium) ion, methylenebis(ethyldimethylammonium) ion, methylenebis(butyldimethylammonium) ion, methylenebis(pentyldimethylammonium) ion, methylenebis(hexyldimethylammonium) ion, methylenebis(octyldimethylammonium) ion, ethylenebis(trimethylammonium) ion, ethylenebis(triethylammonium) ion, ethylenebis(tripropylammonium) ion, ethylenebis(tributylammonium) ion, ethylenebis(tripentylammonium) ion, ethylenebis(trihexylammonium) ion, ethylenebis(trioctylammonium) ion, ethylenebis(ethyldimethylammonium) ion, ethylenebis(butyldimethylammonium) ion, ethylenebis(pentyldimethylammonium) ion, ethylenebis(hexyldimethylammonium) ion, ethylenebis(octyldimethylammonium) ion, trimethylenebis(trimethylammonium) ion, trimethylenebis(triethylammonium) ion, trimethylenebis(tripropylammonium) ion, trimethylenebis(tributylammonium) ion, trimethylenebis(tripentylammonium) ion, trimethylenebis(trihexylammonium) ion, trimethylenebis(trioctylammonium) ion, trimethylenebis(ethyldimethylammonium) ion, trimethylenebis(butyldimethylammonium) ion, trimethylenebis(pentyldimethylammonium) ion, trimethylenebis(hexyldimethylammonium) ion, trimethylenebis(octyldimethylammonium) ion, and the like.

Preferable specific example of biscation represented by the general formula [20] includes, for example, methylenebis(trimethylphosphonium) ion, methylenebis(triethylphosphonium) ion, methylenebis(tripropylphosphonium) ion, methylenebis(tributylphosphonium) ion, methylenebis(tricyclohexylphosphonium) ion, and the like.

Preferable specific other biscation includes, for example, quinolinium ion such as methylenebisquinolinium ion, methylenebis(2-methylquinolinium) ion, methylenebis(3-methylquinolinium) ion, methylenebis(4-methylquinolinium) ion, methylenebis(6-ethylquinolinium) ion, methylenebis(6-isopropylquinolinium) ion.

Preferable specific example of anion moiety in the general formula [1] to [4] includes, for example, allylsulfonate, 1-methylallylsulfonate, 2-methylallylsulfonate, 2-butenylsulfonate, 3-methyl-2-butenylsulfonate, 2-methyl-2-butenylsulfonate, 2,3-dimethyl-2-butenylsulfonate, 1,2,3-trimethyl-2-butenylsulfonate, 3-butenylsulfonate, 1-ethylallylsulfonate, 2-ethylallylsulfonate, 2-pentenylsulfonate, 3-ethyl-2-pentenylsulfonate, 1-propylallylsulfonate, 2-propylallylsulfonate, 2-hexenylsulfonate, 3-propyl-2-hexenylsulfonate, 1-butylallylsulfonate, 2-butylallylsulfonate, 2-heptenylsulfonate, 3-butyl-2-heptenylsulfonate, cyclohexenesulfonate, and the like, among them, allylsulfonate or 2-methylallylsulfonate is preferable, particularly, allylsulfonate is more preferable.

Preferable specific example of ionic liquid represented by the general formula [3] includes, for example, imidazolium cation-containing allylsulfonates such as 3-methylimidazolium allylsulfonate, 1,3-dimethylimidazolium allylsulfonate, 1-ethyl-3-methylimidazolium allylsulfonate, 1-propyl-3-methylimidazolium allylsulfonate, 1-isopropyl-3-methylimidazolium allylsulfonate, 1-butyl-3-methylimidazolium allylsulfonate, 1-allyl-3-methylimidazolium allylsulfonate, 1-allyl-3-ethylimidazolium allylsulfonate, 1-allyl-3-butylimidazolium allylsulfonate, 1,3-dimethylimidazolium 2-methylallylsulfonate, 1-ethyl-3-methylimidazolium 2-methylallylsulfonate, 1,3-dimethylimidazolium 2-butenylsulfonate, 1,3-dimethylimidazolium 3-methyl-2-butenylsulfonate, 1,3-dimethylimidazolium cyclohexenesulfonate, 1,3-dimethylimidazolium 3-butenylsulfonate, 1-butyl-2,3-dimethylimidazolium allylsulfonate, 1-ethyl-2,3-dimethylimidazolium allylsulfonate, 1-butyl-3-ethylimidazolium allylsulfonate, 1,3-dibutylimidazolium allylsulfonate, 1-butyl-3-methylimidazolium 2-methylallylsulfonate, 1-butyl-3-methylimidazolium 2-butenylsulfonate, 1-butyl-3-methylimidazolium 3-methyl-2-butenylsulfonate, 1-butyl-3-methylimidazolium cyclohexenesulfonate, 1-butyl-3-methylimidazolium 3-butenylsulfonate, 1,2,3-trimethylimidazolium allylsulfonate, 1,2-dimethyl-3-ethylimidazolium allylsulfonate, 1,2-dimethyl-3-butylimidazolium allylsulfonate, 1,2,3-trimethylimidazolium 2-methylallylsulfonate, 1,2,3-trimethylimidazolium 2-butenylsulfonate, 1,2,3-trimethylimidazolium 3-methyl-2-butenylsulfonate, 1,2,3-trimethylimidazolium cyclohexenesulfonate, 1,2,3-trimethylimidazolium 3-butenylsulfonate; for example, pyridinium cation-containing allylsulfonates such as pyridinium allylsulfonate, 1-methylpyridinium allylsulfonate, 1-ethylpyridinium allylsulfonate, 1-propylpyridinium allylsulfonate, 1-isopropylpyridinium allylsulfonate, 1-butylpyridinium allylsulfonate, 1-allylpyridinium allylsulfonate, 1-ethyl-4-methoxypyridinium allylsulfonate, 1-methylpyridinium 2-methylallylsulfonate, 1-ethylpyridinium 2-methylallylsulfonate, 1-ethyl-4-methoxypyridinium 2-methylallylsulfonate, 1-methylpyridinium 2-butenylsulfonate, 1-ethyl-4-methoxypyridinium 2-butenylsulfonate, 1-methylpyridinium 3-methyl-2-butenylsulfonate, 1-ethyl-4-methoxypyridinium 3-methyl-2-butenylsulfonate, 1-methylpyridinium cyclohexenesulfonate, 1-ethyl-4-methoxypyridinium cyclohexenesulfonate, 1-methylpyridinium 3-butenylsulfonate, 1-ethyl-4-methoxypyridinium 3-butenylsulfonate; for example, piperidinium cation-containing allyl sulfonates such as 1,1-dimethylpiperidinium allylsulfonate, 1-ethyl-1-methylpiperidinium allylsulfonate, 1-butyl-1-methylpiperidinium allylsulfonate, 1-(hydroxyethyl)-1-methylpiperidinium allylsulfonate, 1,1-dimethylpiperidinium 2-methylallylsulfonate, 1-ethyl-1-methylpiperidinium 2-methylallylsulfonate, 1,1-dimethylpiperidinium 2-butenylsulfonate, 1-ethyl-1-methylpiperidinium 2-butenylsulfonate, 1,1-dimethylpiperidinium 3-methyl-2-butenylsulfonate, 1-ethyl-1-methylpiperidinium 3-methyl-2-butenylsulfonate, 1,1-dimethylpiperidinium cyclohexenesulfonate, 1-ethyl-1-methylpiperidinium cyclohexenesulfonate, 1,1-dimethylpiperidinium 3-butenylsulfonate, 1-ethyl-1-methylpiperidinium 3-butenylsulfonate; for example, pyrrolidinium cation-containing allylsulfonates such as 1,1-dimethylpyrrolidinium allylsulfonate, 1-ethyl-1-methylpyrrolidinium allylsulfonate, 1-butyl-1-methylpyrrolidinium allylsulfonate, 1-(hydroxyethyl)-1-methylpyrrolidinium allylsulfonate, 1,1-dimethylpyrrolidinium 2-methylallylsulfonate, 1-ethyl-1-methylpyrrolidinium 2-methylallylsulfonate, 1,1-dimethylpyrrolidinium 2-butenylsulfonate, 1-ethyl-1-methylpyrrolidinium 2-butenylsulfonate, 1,1-dimethylpyrrolidinium 3-methyl-2-butenylsulfonate, 1-ethyl-1-methylpyrrolidinium 3-methyl-2-butenylsulfonate, 1,1-dimethylpyrrolidinium cyclohexenesulfonate, 1-ethyl-1-methylpyrrolidinium cyclohexenesulfonate, 1,1-dimethylpyrrolidinium 3-butenylsulfonate, 1-ethyl-1-methylpyrrolidinium 3-butenylsulfonate; for example, morpholinium cation-containing allylsulfonates such as N,N-dimethylmorpholinium allylsulfonate, N-ethyl-N-methylmorpholinium allylsulfonate, N,N-diethylmorpholinium allylsulfonate, N-propyl-N-methylmorpholinium allylsulfonate, N,N-dipropylmorpholinium allylsulfonate, N-butyl-N-methylmorpholinium allylsulfonate, N,N-dibutylmorpholinium allylsulfonate, N-ethyl-N-methylmorpholinium 2-methylallylsulfonate, N-ethyl-N-methylmorpholinium 2-butenylsulfonate, N-ethyl-N-methylmorpholinium 3-methyl-2-butenylsulfonate, N-ethyl-N-methylmorpholinium cyclohexenesulfonate, N-ethyl-N-methylmorpholinium 3-butenylsulfonate; for example, ammonium cation-containing allylsulfonates such as triethylmethylammonium allylsulfonate, ethyltrimethylammonium allylsulfonate, hexyltrimethylammonium allylsulfonate, trimethyloctylammonium allylsulfonate, tetraethylammonium allylsulfonate, butyltriethylammonium allylsulfonate, methyltriethylammonium 2-methylallylsulfonate, methyltriethylammonium 2-butenylsulfonate, methyltriethylammonium 3-methyl-2-butenylsulfonate, methyltriethylammonium cyclohexenesulfonate, methyltriethylammonium 3-butenylsulfonate, methyltributylammonium allylsulfonate, ethyltributylammonium allylsulfonate, tetrabutylammonium allylsulfonate, methyltributylammonium 2-methylallylsulfonate, methyltributylammonium 2-butenylsulfonate, methyltributylammonium 3-methyl-2-butenylsulfonate, methyltributylammonium cyclohexenesulfonate, methyltributylammonium 3-butenylsulfonate; for example, phosphonium cation-containing allylsulfonates such as tetramethylphosphonium allylsulfonate, tetraethylphosphonium allylsulfonate, tetrapropylphosphonium allylsulfonate, tetrabutylphosphonium allylsulfonate, ethyltrimethylphosphonium allylsulfonate, triethylmethylphosphonium allylsulfonate, tricyclohexylmethylphosphonium allylsulfonate, tributylmethylphosphonium allylsulfonate, butyltriethylphosphonium allylsulfonate; among them, for example, pyridinium cation-containing allylsulfonates such as pyridinium allylsulfonate, 1-methylpyridinium allylsulfonate, 1-ethylpyridinium allylsulfonate, 1-propylpyridinium allylsulfonate, 1-isopropylpyridinium allylsulfonate, 1-butylpyridinium allylsulfonate, 1-ethyl-4-methoxypyridinium allylsulfonate, 1-methylpyridinium 2-methylallylsulfonate, 1-ethylpyridinium 2-methylallylsulfonate; for example, imidazolium cation-containing allylsulfonates such as 3-methylimidazolium allylsulfonate, 1,3-dimethylimidazolium allylsulfonate, 1-ethyl-3-methylimidazolium allylsulfonate, 1-propyl-3-methylimidazolium allylsulfonate, 1-isopropyl-3-methylimidazolium allylsulfonate, 1-butyl-3-methylimidazolium allylsulfonate, 1-allyl-3-methylimidazolium allylsulfonate, 1-allyl-3-ethylimidazolium allylsulfonate, 1-allyl-3-butylimidazolium allylsulfonate, 1,3-dimethylimidazolium 2-methylallylsulfonate, 1-ethyl-3-methylimidazolium 2-methylallylsulfonate, 1-butyl-2,3-dimethylimidazolium allylsulfonate, 1-ethyl-2,3-dimethylimidazolium allylsulfonate; for example, ammonium cation-containing allylsulfonates such as triethylmethylammonium allylsulfonate, ethyltrimethylammonium allylsulfonate, hexyltrimethylammonium allylsulfonate, trimethyloctylammonium sulfonate; for example, piperidinium cation-containing allylsulfonates such as 1,1-dimethylpiperidinium allylsulfonate, 1-ethyl-1-methylpiperidinium allylsulfonate, 1-butyl-1-methylpiperidinium allylsulfonate, 1-(hydroxyethyl)-1-methylpiperidinium allylsulfonate; for example, pyrrolidinium cation-containing allylsulfonates such as 1,1-dimethylpyrrolidinium allylsulfonate, 1-ethyl-1-methylpyrrolidinium allylsulfonate, 1-butyl-1-methylpyrrolidinium allylsulfonate; for example, morpholinium cation-containing allylsulfonates such as N,N-dimethylmorpholinium allylsulfonate, N-ethyl-N-methylmorpholinium allylsulfonate; for example, phosphonium cation-containing allylsulfonate such as tributylmethylphosphonium allylsulfonate is preferable, more preferably, for example, imidazolium cation-containing allylsulfonates such as 1-ethyl-4-methoxypyridinium allylsulfonate, 1-ethyl-3-methylimidazolium allylsulfonate, 1-propyl-3-methylimidazolium allylsulfonate, 1-isopropyl-3-methylimidazolium allylsulfonate, 1-butyl-3-methylimidazolium allylsulfonate, 1-allyl-3-methylimidazolium allylsulfonate, 1-allyl-3-ethylimidazolium allylsulfonate, 1-allyl-3-butylimidazolium allylsulfonate; for example, pyrrolidinium cation-containing allylsulfonate such as 1-ethyl-1-methylpyrrolidinium allylsulfonate; for example, morpholinium cation-containing allylsulfonates such as N,N-dimethylmorpholinium allylsulfonate, N-ethyl-N-methylmorpholinium allylsulfonate; for example, piperidinium cation-containing allylsulfonate such as 1-(hydroxyethyl)-1-methylpiperidinium allylsulfonate, and the like are included.

Preferable specific example of ionic liquid represented by the general formula [4] includes, for example, methylenebis(trimethylammonium) allylsulfonate, methylenebis(triethylammonium) allylsulfonate, methylenebis(tributylammonium) allylsulfonate, methylenebis(1-methylpiperidinium) allylsulfonate, methylenebispyridinium allylsulfonate, methylenebispyridinium 2-methylallylsulfonate, methylenebispyridinium 2-butenylsulfonate, methylenebispyridinium 3-methyl-2-butenylsulfonate, methylenebispyridinium cyclohexenesulfonate, methylenebispyridinium 3-butenylsulfonate, methylenebis(3,5-dimethylpyridinium) allylsulfonate, methylenebis(3-methylpyridinium) allylsulfonate, methylenebis(1,2-dimethylimidazolium) allylsulfonate, methylenebis(1-butylimidazolium) allylsulfonate, methylenebis(1-methylimidazolium) allylsulfonate, ethylenebispyridinium allylsulfonate, ethylenebis(3-methylpyridinium) allylsulfonate, ethylenebis(1-butylimidazolium)allylsulfonate, ethylenebis(1-methylimidazolium)allylsulfonate, trimethylenebispyridinium allylsulfonate, trimethylenebis(3,5-dimethylpyridinium) allylsulfonate, trimethylenebis(3-pyridinium) allylsulfonate, trimethylenebis(1-butylimidazolium) allylsulfonate, trimethylenebis(1-methylimidazolium) allylsulfonate, tetramethylenebispyridinium allylsulfonate, tetramethylenebis(3,5-dimethylpyridinium) allylsulfonate, tetramethylenebis(3-pyridinium) allylsulfonate, tetramethylenebis(1-butylimidazolium) allylsulfonate, tetramethylenebis(1-methylimidazolium) allylsulfonate, and the like, among them, for example, methylenebispyridinium allylsulfonate, methylenebispyridinium 2-methylallylsulfonate, methylenebis (1-methylimidazolium) allylsulfonate, and the like are preferable.

The ionic liquid represented by the general formula [1] of the present invention is a salt (a molten salt) existing as liquid usually at 100° C. or less, in preferable order, at 80° C. or less, at 50° C. or less, at 25° C. or less.

In addition, the ionic liquid represented by the general formula [4] of the present invention is a salt (a molten salt) existing as liquid usually at 200° C. or less, in preferable order, at 180° C. or less, 170° C. or less, 160° C. or less, 120° C. or less.

Viscosity of the ionic liquid represented by the general formula [1] of the present invention is preferable as low as possible considering from ease of handling, and it is preferably 1000 mPa·s or less at 25° C., in preferable order, 800 mPa·s or less, 500 mPa·s or less, 300 mPa·s or less. In addition, it is usually 400 mP·s or less at 40° C., in preferable order, 300 mPa·s or less, 200 mPa·s or less, 150 mPa·s or less.

The ionic liquid of the present invention represented by the general formula [3] may be produced, for example, as described below. That is, allylsulfonic acid ester represented by the general formula [21]

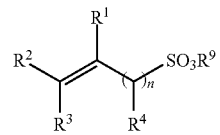

[21]

(wherein $R^1$ to $R^4$, $R^9$ and n are the same as the above-described) and 1 to 1.5 times in moles of the compound represented by the general formula [22] relative to said allylsulfonic acid ester

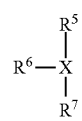

[22]

(wherein $R^5$ to $R^7$ and X are the same as the above-described) are mixed, and are reacted without solvent or in the appropriate solvent at 0 to 200° C. for 0.5 to 24 hours to obtain the desired ionic liquid represented by the general formula [3].

As a reaction solvent which is used, non-aqueous solvent is preferable, specifically, it includes, for example, aliphatic hydrocarbons such as hexane, heptane, octane, isooctane, nonane, decane, undecane, dodecane, tridecane, tetradecane, pentadecane, hexadecane, heptadecane, octadecane, cyclohexane, methylcyclohexane, ethylcyclohecane, or the mixture thereof (for example, paraffin, mineral sprit, and the like); for example, halogenated hydrocarbons such as chloromethylene, bromomethylene, 1,2-dichloroethane, chloroform; for example, aromatic hydrocarbons such as benzene, toluene, xylene; for example, carbonates such as dimethyl carbonate, diethyl carbonate, ethylene carbonate, propylene carbonate; for example, esters such as methyl acetate, ethyl acetate, butyl acetate; for example, ketones such as acetone, methyl ethyl ketone; for example, ethers such as diethyl ether, isopropyl ether, cyclopentyl methyl ether, tetrahydrofuran, dioxane; for example, acetonitrile; dimethylformamide; dimethylacetamide; dimethylsulfoxide; and the like. These may be used alone or appropriately in combination of two or more kinds.

Reaction temperature is usually 0 to 200° C., preferably 20 to 120° C.

Reaction time is usually 0.5 to 24 hours, preferably 0.5 to 12 hours.

As allylsulfonic acid represented by the general formula [21] and the compound represented by the general formula [22], the commercially available product or the compound appropriately synthesized by the usual method may be used.

The ionic liquid represented by the general formula [4] of the present invention may be produced, for example, as described below. That is, disulfonic acid ester represented by the general formula [23]

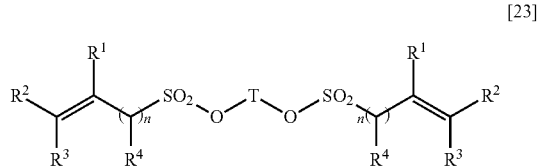

[23]

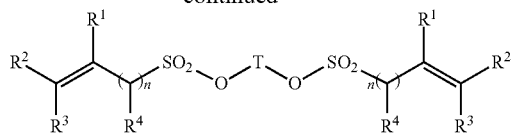

[23]

(wherein $R^1$ to $R^4$, T, and n are the same as the above-described) and 2 to 5 times in moles of the amine compound represented by the general formula [22'] relative to said disulfonic acid ester

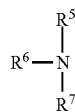

[22']

(wherein $R^5$ to $R^7$ is the same as the above-described), are mixed, and are reacted without solvent or in the appropriate solvent at 0 to 200° C. for 0.5 to 24 hours to obtain the desired ionic liquid represented by the general formula [4].

As a reaction solvent which is used, nonaqueous solvent is preferable, specifically, it includes, for example, aliphatic hydrocarbons such as hexane, heptane, octane, isooctane, nonane, decane, undecane, dodecane, tridecane, tetradecane, pentadecane, hexadecane, heptadecane, octadecane, cyclohexane, methylcyclohexane, ethylcyclo hexane, or the mixture thereof (for example, paraffin, mineral sprit, and the like); for example, halogenated hydrocarbons such as chloromethylene, bromomethylene, 1,2-dichloroethene, chloroform; for example, aromatic hydrocarbons such as benzene, toluene, xylene; for example, carbonates such as dimethyl carbonate, diethyl carbonate, ethylene carbonate, propylene carbonate; for example, esters such as methyl acetate, ethyl acetate, butyl acetate; for example, ketones such as acetone, methyl ethyl ketone; for example, ethers such as diethyl ether, isopropyl ether, cyclopentyl methyl ether, tetrahydrofuran, dioxane; for example, acetonitrile; dimethylformamide; dimethylacetamide; dimethylsulfoxide; and the like. These may be used alone or appropriately in combination of two or more kinds.

Reaction temperature is usually 0 to 200° C., preferably 20 to 120°C.

Reaction time is usually 0.5 to 24 hours, preferably 0.5 to 12 hours.

Post-treatment after reaction may be carried out according to the usual post-treatment method in the art.

As amine compound represented by the general formula [22'], the commercially available product or the one appropriately synthesized by the usual method may be used.

Disulfonic acid ester represented by the general formula [23] may be synthesized according to the usual method (for example, WO 2008/032463 and the like), specifically, for example, it may be produced as follows:

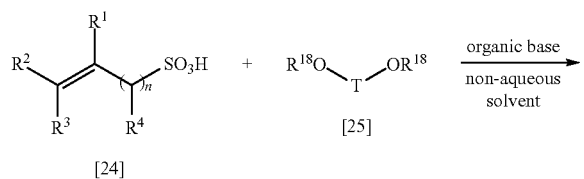

{wherein 2 pieces of $R^{18}$ each independently represent sulfonyl groups represented by the general formula [26]

$$—SO_2—R^{19}$$ [26]

(wherein $R^{19}$ represents a halogen atom, a haloalkyl group, an alkoxy group, or an alkyl group or an aryl group which may have substituent), or an acyl group represented by the general formula [27]

$$—COR^{20}$$ [27]

(wherein $R^{20}$ represents an alkyl group or an aryl group which may have substituent), $R^1$ to $R^4$, T and n are the same as the above-described}.

A halogen atom represented by $R^{19}$ in the general formula [26] includes, for example, a fluorine atom, a chlorine atom, a bromine atom, an iodine atom, and the like.

A haloalkyl group represented by $R^{19}$ may be any of a straight chain, a branched, or an cyclic group, it includes the one in which a part or all of hydrogen atoms of alkyl group having usually 1 to 12 carbon atoms, preferably 1 to 6, more preferably 1 to 3, are substituted by halogen atoms (for example, a fluorine atom, a bromine atom, a chlorine atom, an iodine atom, and the like are included), and specifically, it includes, for example, a fluoromethyl group, a chloromethyl group, a bromomethyl group, an iodomethyl group, a trifluoromethyl group, a trichloromethyl group, a tribromomethyl group, a 2-fluoroethyl group, a 2-chloroethyl group, 2-bromoethyl group, a pentaiodoethyl group, a pentachloroethyl group, a pentafluoroethyl group, a pentabromoethyl group, a 3-fluoropropyl group, a 3-chloropropyl group, a 3-bromopropyl group, a trifluoropropyl group, a trichloropropyl group, a tribromopropyl group, a di(trifluoromethyl)methyl group, a di(trichloromethyl)methyl group, a di(tribromomethyl)methyl group, a heptafluoropropyl group, a heptachloropropyl group, a 4-fluorobutyl group, a 4-chlorobutyl group, a 4-bromobutyl group, a nonafluorobutyl group, a nonachlorobutyl group, a nonabromobutyl group, a 5-fluoropentyl group, a 5-chloropentyl group, a 5-bromopentyl group, a 2,2,3,3,4,4,5,5-octafluoropentyl group($—CH_2(CF_2)_4H$), a 2,2,3,3,4,4,5,5-octachloropentyl group($—CH_2(CCl_2)_4H$), a 2,2,3,3,4,4,5,5-octabromopentyl group($—CH_2(CBr_2)_4H$), a perfluoropentyl group, a perchloropentyl group, a perbromopentyl group, a 6-fluorohexyl group, a 6-chlorohexyl group, a 6-bromohexyl group, a perfluorohexyl group, a perchlorohexyl group, a perbromohexyl group, a perfluoroheptyl group, perchloroheptyl group, a perbromoheptyl group, a perfluorooctyl group, a perchlorooctyl group, a perbromooctyl group, a perfluorononyl group, a perchlorononyl group, a perbromononyl group, a 3,3,4,4,5,5,6,6,7,7,8,8,9,9,10,10,10-heptadecafluorodecyl group ($—(CH_2)_2(CF_2)_7CF_3$), a 3,3,4,4,5,5,6,6,7,7,8,8,9,9,10,10,10-heptadecachlorodecyl group ($—(CH_2)_2(CCl_2)_7CCl_3$), a 3,3,4,4,5,5,6,6,7,7,8,8,9,9,10,10,10-heptadecabromodecyl group ($—(CH_2)_2(CBr_2)_7CBr_3$), a perfluorodecyl group, a perchlorodecyl group, a perbromodecyl group, a perfluoroundecyl group, a perchloroundecyl group, a perbromoundecyl group, a perfluorododecyl group, a perchlorododecyl group, a perbromododecyl group, and the like, among them, a perfluoroalkyl group having 1 to 3 carbon atoms is preferable, particularly, a trifluoromethyl group is more preferable.

An alkoxy group represented by $R_{19}$ may be any of a straight chain, a branched, or a cyclic group, and includes the one having usually 1 to 12 carbon atoms, preferably 1 to 6, more preferably 1 to 3, and specifically, it includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a 1-methylpentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group, a neododecyloxy group, a cyclopropoxy group, a cyclobutoxy group, a cyclopentyloxy group, a cyclohexyloxy group, a cycloheptyloxy group, a cyclooctyloxy group, a cyclononyloxy group, cyclodecyloxy group, a cycloundecyloxy group, cyclododecyloxy group, and the like, among them, for example, a methoxy group, an ethoxy group, a n-propoxy group and the like are preferable.

An alkyl group of alkyl group which may have substituent represented by $R^{19}$ and $R^{20}$
may be any of a straight chain, a branched or a cyclic group, and it includes the one having usually 1 to 12 carbon atoms, preferably 1 to 6, more preferably 1 to 3, specifically, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isodoecyl group, a sec-dodecyl group, a tert-dodecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, and the like, among them, for example, a methyl group, an ethyl group, a n-propyl group are preferable, particularly, a methyl group is more preferable.

Aryl group of aryl group which may have substituent represented by $R^{19}$ and $R^{20}$ includes the one having 6 to 14 carbon atoms, preferably 6 to 10, and includes specifically, for example, a phenyl group, a naphthyl group, a phenanthryl group, an anthryl group and the like.

Substituent of alkyl group which may have substituent represented by $R^{19}$ includes, for example, an alkoxy group having 1 to 12 carbon atoms, an acyl group, a nitro group, a hydroxyl group, a carboxyl group, a cyano group, a formyl group, and the like.

Substituent of alkyl group represented by $R^{20}$ which may have substituent includes, for example, a halogen atom, alkoxy group having 1 to 12 carbon atoms, an acyl group, a nitro group, a hydroxyl group, a carboxyl group, a cyano group, a formyl group, and the like.

Substituent of aryl group represented by $R^{19}$ and $R^{20}$ which may have substituent includes, for example, a halogen atom, an alkyl group having 1 to 12 carbon atoms, an alkoxy group having 1 to 12 carbon atoms, an acyl group, a nitro group, a hydroxyl group, a carboxyl group, a cyano group, a formyl group, and the like.

A halogen atom exemplified as substituent includes, for example, a fluorine atom, a chlorine atom, a bromine atom, an iodine atom, and the like.

An alkoxy group having 1 to 12 carbon atoms exemplified as substituent may be any of a straight chain, a branched, or an cyclic group, includes the one having usually 1 to 12 carbon atoms, preferably 1 to 6, more preferably 1 to 3, and specifically, it includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group, a neododecyloxy group, a cyclopropoxy group, a cyclobutoxy group, a cyclopentyloxy group, a cyclohexyloxy group, a cycloheptyloxy group, a cyclooctyloxy group, a cyclononyloxy group, a cyclodecyloxy group, a cycloundecyloxy group, a cyclododecyloxy group, and the like.

Acyl group exemplified as substituent includes the one derived from carboxylic acid having usually 2 to 20 carbon atoms, and specifically, it includes, for example, the one derived from aliphatic carboxylic acid such as an acetyl group, a propionyl group, a butyryl group, an isobutyryl group, a valeryl group, an isovaleryl group, a pivaloyl group, a hexanoyl group, a heptanoyl group, an octanoyl group, a nonanoyl group, a decanoyl group, a dodecanoyl group, a tridecanoyl group, a tetradecanoyl group, a pentadecanoyl group, a hexadecanoyl group, a heptadecanoy group, an octadecanoy group, a nonadecanoy group, an icosanoyl group; for example, the one derived from aromatic carboxylic acid such as a benzoyl group, a naphthoyl group, and the like.

An alkyl group having 1 to 12 carbon atoms exemplified as substituent may be any of a straight chain, a branched, or a cyclic group, includes the one having usually 1 to 12 carbon atoms, preferably 1 to 6, more preferably 1 to 3, and specifically, it includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyloxy group, a tert-undecyloxy group, neoundecyloxy group, n-dodecyloxy group, an isododecyloxy group, a sec-dodecyloxy group, a tert-dodecyloxy group, a neododecyloxy group, a cyclopropoxy group, a cyclobutoxy group, a cyclopentyloxy group, a cyclohexyloxy group, a cycloheptyloxy group, cyclooctyloxy group, cyclononyloxy group, cyclodecyloxy group, cycloundecyloxy group, cyclododecyloxy group and the like.

As a production method of disulfonic acid ester represented by the general formula [23], for example, allyl sulfonic acid represented by the general formula [24] and 1 to 4 times in moles of organic base and 0.2 to 0.5 times in moles of the compound represented by the general formula [25] relative to said sulfonic acid are added in the appropriate solvent at 0 to 150° C., then are reacted by stirring for 0.5 to 12 hours to obtain the desired disulfonic acid ester represented by the general formula [23].

It should be noted that, sulfonic acid represented by the general formula [24] and said organic base have been mixed in the appropriate solvent in advance, and after removed solvent by condensation etc. if necessary, in addition, appropriate poor solvent has been added to precipitate salt, if necessary, then this was filtered to isolate the salt formed by th sulfonic acid represented by the general formula [24] and organic base, then the isolated salt may be reacted with the compound represented by the general formula [25].

As the reaction solvent used in this process, non-aqueous solvent is preferable, specifically, it includes, for example, aliphatic hydrocarbons such as hexane, heptane, octane, isooctane, nonane, decane, undecane, dodecane, tridecane, tetradecane, pentadecane, hexadecane, heptadecane, octadecane, cyclohexane, methylcyclohexane, ethylcyclohecane, or the mixture thereof (for example, paraffin, mineral sprit and the like); for example, halogenated hydrocarbons such as chloromethylene, bromomethylene, 1,2-dichloroethane, chloroform; for example, aromatic hydrocarbons such as benzene, toluene, xylene; for example, carbonates such as dimethyl carbonate, diethyl carbonate, ethylene carbonate, propylene carbonate; for example, esters such as methyl acetate, ethyl acetate, butyl acetate; for example, ketones such as acetone, methyl ethyl ketone; for example, ethers such as diethyl ether, isopropyl ether, cyclopentyl methyl ether, tetrahydrofuran, dioxane; for example, acetonitrile; dimethylformamide; dimethylacetamide; dimethylsulfoxide; and the like. These may be used alone, or appropriately in combination of two or more kinds.

Combination, in which reaction solvent is used as mixed solvent, includes, for example, combination of acetonitrile and cyclohexane, and acetonitrile and toluene, and the like.

Reaction temperature is usually 0 to 150° C., preferably 20 to 100° C.

Reaction time is usually 0.5 to 24 hours, preferably 0.5 to 12 hours.

In addition, poor solvent, which is used to precipitate the salt formed by sulfonic acid represented by the general formula [24] and organic base in advance, may be any of the solvent, which reduce the solubility of said salt, that is, is allowed to precipitate said salt, and specifically, for example, it includes aliphatic hydrocarbons such as hexane, heptane, octane, isooctane, nonane, decane, undecane, dodecane, tridecane, tetradecane, pentadecane, hexadecane, heptadecane, octadecane, cyclohexane, methylcyclohexane, ethylcyclohecane, or the mixture thereof (for example, paraffin, mineral sprit and the like); for example, halogenated hydrocarbons such as chloromethylene, bromomethylene, 1,2-dichloroethane, chloroform; for example, aromatic hydrocarbons such as benzene, toluene, xylene; for example, carbonates such as dimethyl carbonate, diethyl carbonate, ethylene carbonate, propylene carbonate; for example, esters such as methyl acetate, ethyl acetate, butyl acetate; for example, ketones such as acetone, methyl ethyl ketone; for example, ethers such as diethyl ether, isopropyl ether, cyclopentyl methyl ether, tetrahydrofuran, dioxane; for example, alcohols such as methanol, ethanol, n-propanol, isopropanol; acetonitrile, and the like. These may be used alone, or appropriately in combination of two or more kinds.

Specific example of the compound represented by the general formula [22] includes, for example, tertiary amines, imidazoles, pyridines, piperidines, pyrrolidines, pyrazoles, morpholines, quinolones, phosphines, and the like.

Specific example of amine compound represented by the general formula [22'] includes, for example, tertiary amines, imidazoles, pyridines, piperidines, pyrrolidines, pyrazoles, morpholines, quinolones, and the like.

Preferable specific example of tertiary amines represented by the general formula [22] and [22'] includes, for example, tertiary alkylamines such as trimethylamine, triethylamine, tri-n-propylamine, tri-isopropylamine, tri-n-butylamine, tri-isobutylamine, tri-sec-butylamine, tri-tert-butylamine, tri-n-pentylamine, tri-isopentylamine, tri-sec-pentylamine, tri-tert-pentylamine, tri-neopentylamine, trihexylamine, tri-isohexylamine, tri-sec-hexylamine, tri-tert-hexylamine, tri-neohexylamine, tricyclopropylamine, tricyclobutylamine, tricyclopentylamine, tricyclohexylamine, dimethylethylamine, di-isopropylethylamine; for example, tertiary aryl amines such as triphenylamine, trinaphthylamine; for example, tertiary aralkylamines such as tribenzylamine, and the like.

Preferable specific example of imidazoles represented by the general formula [22] and [22'] includes, for example, 1-methylimidazole, 1-ethylimidazole, 1-propylimidazole, 1-butylimidazole, 1-pentylimidazole, 1-hexylimidazole, 1-heptylimidazole, 1-octylimidazole, 1-nonylimidazole, 1-decylimidazole, 1-undecylimidazole, 1-dodecylimidazole, and the like.

Preferable specific example of pyridines represented by the general formula [22] and [22'] includes, for example, 2-methylpyridine, 3-methylpyridine, 4-methylpyridine, 5-methylpyridine, 6-methylpyridine, 2-ethylpyridine, 3-ethylpyridine, 4-ethylpyridine, 5-ethylpyridine, 6-ethylpyridine, 2-propylpyridine, 3-propylpyridine, 4-propylpyridine, 5-propylpyridine, 6-propylpyridine, 2-butylpyridine, 3-butylpyridine, 4-butylpyridine, 5-butylpyridine, 6-butylpyridine, 2-pentylpyridine, 3-pentylpyridine, 4-pentylpyridine, 5-pentylpyridine, 6-pentylpyridine, 2-hexylpyridine, 3-hexylpyridine, 4-hexylpyridine, 5-hexylpyridine, 6-hexylpyridine, 2-heptylpyridine, 3-heptylpyridine, 4-heptylpyridine, 5-heptylpyridine, 6-heptylpyridine, 2-octylpyridine, 3-octylpyridine, 4-octylpyridine, 5-octylpyridine, 6-octylpyridine, 2-nonylpyridine, 3-nonylpyridine, 4-nonylpyridine, 5-nonylpyridine, 6-nonylpyridine, 2-decylpyridine, 3-decylpyridine, 4-decylpyridine, 5-decylpyridine, 6-decylpyridine, 2-undecylpyridine, 3-undecylpyridine, 4-undecylpyridine, 5-undecylpyridine, 6-undecylpyridine, 2-dodecylpyridine, 3-dodecylpyridine, 4-dodecylpyridine, 5-dodecylpyridine, 6-dodecylpyridine, 2,3-lutidine, 2,4-lutidine, 2,5-lutidine, 2,6-lutidine, 3,4-lutidine, 3,5-lutidine, 2,4,6-collidine, α-collidine (4-ethyl-2-methylpyridine), β-collidine (3-ethyl-4-methylpyridine), γ-collidine (2,4,6-collidine), and the like.

Preferable specific example of piperidines represented by the general formula [22] and [22'] includes, for example, 1-methylpiperidine, 1-ethylpiperidine, 1-propylpiperidine, 1-butylpiperidine, 1-pentylpiperidine, 1-hexylpiperidine, 1-heptylpiperidine, 1-octylpiperidine, 1-nonylpiperidine, 1-decylpiperidine, 1-undecylpiperidine, 1-dodecylpiperidine, and the like.

Preferable specific example of pyrrolidines represented by the general formula [22] and [22'] includes, for example, 1-methylpyrrolidine, 1-ethylpyrrolidine, 1-propylpyrrolidine, 1-butylpyrrolidine, 1-pentylpyrrolidine, 1-hexylpyrrolidine, 1-heptylpyrrolidine, 1-octylpyrrolidine, 1-nonylpyrrolidine, 1-decylpyrrolidine, 1-undecylpyrrolidine, 1-dodecylpyrrolidine, and the like.

Preferable specific example of pyrazoles represented by the general formula [22] and [22'] includes, for example, 1-methylpyrazole, 1-ethylpyrazole, 1-propylpyrazole, 1-butylpyrazole, 1-pentylpyrazole, 1-hexylpyrazole, 1-heptylpyrazole, 1-octylpyrazole, 1-nonylpyrazole, 1-decylpyrazole, 1-undecylpyrazole, 1-dodecylpyrazole, 1-methyl-3,5-dimethylpyrazole, 1-ethyl-3,5-dimethylpyrazole, 1-propyl-3,5-dimethylpyrazole, 1-butyl-3,5-dimethylpyrazole, 1-pentyl-3,5-dimethylpyrazole, 1-hexyl-3,5-dimethylpyrazole, 1-heptyl-3,5-dimethylpyrazole, 1-octyl-3,5-dimethylpyrazole, 1-nonyl-3,5-dimethylpyrazole, 1-decyl-3,5-dimethylpyrazole, 1-undecyl-3,5-dimethylpyrazole, 1-dodecyl-3,5-dimethylpyrazole, and the like.

Preferable specific example of morpholines represented by the general formula [22] and [22'] includes, for example, N-methylmorpholine, N-ethylmorpholine, N-propylmorpholine, N-butylmorpholine, and the like.

Preferable specific example of quinolines represented by the general formula [22] and [22'] includes, for example, quinolone, 2-methylquinoline, 3-methylquinoline, 4-methylquinoline, 6-ethylquinoline, 6-isopropylquinoline, and the like.

Preferable specific example of phosphines represented by the general formula [22] includes, for example, trimethylphosphine, triethylphosphine, tripropylphosphine, tributylphosphine, tricyclohexylphosphine, and the like.

Post-treatment after reaction may be carried out according to the usual post-treatment method in the art.

The ionic liquid of the present invention, since anion is derived from allylsulfonic acid, has no problem that for example, adverse effect for the environment, corrosive property and high production cost, and the like, due to halogenic anion, therefore, can be used for wide fields.

In addition, the ionic liquid of the present invention has no problem such that the conventional ionic liquid having non-halogenic anion exhibits low melting point, however, comparatively high viscosity, and further, has low melting point as well as low viscosity, for example, this is suitable for use of lubricant (for example, use for grease composition, rolling apparatus), solvent of chemical reaction, solvent for separation and extraction, reaction catalyst, antibacterial agent, and the like.

The ionic liquid of the present invention can be expected to exhibit excellent ionic conductivity, therefore, can be used, for example, for electrolyte for electrochemical device such as various types of storage device, solar cell, fuel cell etc., or additives thereof (for example, for lithium ion secondary battery, electric bilayer capacitor, solar cell, fuel cell, actuator element), antistatic agent (for example, for adhesive agent, adhesive sheet, conductive rubber), and the like.

In addition, the ionic liquid of the present invention represented by the general formula [3] is expected to improve the ionic conductivity due to existing of 2 ionic sites in molecule, therefore, for example, is suitable for use of electrolyte of electrochemical device.

The present invention will be further specifically described by using Examples and Comparative Examples, however, the present invention is not limited thereto.

EXAMPLE

Viscosity of the desired product was measured by using RE80 type viscometer (manufactured by Toki Sangyo Co., Ltd.) as follows. That is, thermostatic chamber is maintained at 25° C., and 0.5 ml of the sample of the desired product was inserted onto the sample table, and was fixed with plate, then plate was allowed to rotate at constant revolution number (20 rpm), therefore, numerical value in stable state was defined as viscosity.

Example 1

1-Methylpyridinium Allylsulfonate

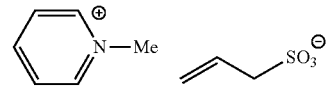

*Me=methyl group

Methyl allylsulfonate (21.4 g, 0.157 mol) synthesized by the conventional method and pyridine (13.1 g, 0.166mol, 1.05 eq) were reacted by stirring for 2 hours at 80° C. After completed the reaction, unreacted pyridine was removed under reduced pressure, crude substance was washed with ethyl acetate several times. The desired product of 1-methylpyridinium allylsulfonate (31.4 g, 0.146 mmol, 93% yield) was obtained by drying by heating under reduced pressure. Melting point was 39° C. Measurement result of $^1$H NMR was shown as follows:

$^1$H NMR (D$_2$O); δ=8.66-8.65 (d, 2H), 8.43-8.39 (t, 1H), 7.94-7.91 (d, 2H), 5.84-5.73 (m, 1H), 5.26-5.22 (m, 2H), 4.27 (s, 3H), 3.51-3.49 (d, 2H).

Example 2

1-Ethylpyridinium Allylsulfonate

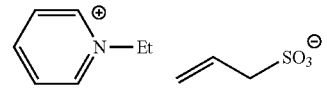

*Et=ethyl group

By the same operation except that ethyl allylsulfonate was used instead of methyl allylsulfonate in Example 1, 1-ethylpyridinium allylsulfonate (33.3 g, 0.145 mol, 95% yield) was obtained. Melting point was 28° C. Measurement result of $^1$H NMR was shown as follows:

¹H NMR (D₂O); δ=8.74-8.73 (d, 2H), 8.43-8.39 (t, 1H), 7.95-7.94 (d, 2H), 5.83-5.73 (m, 1H), 5.26-5.21 (m, 2H), 4.55-4.50 (q, 2H), 3.51-3.49 (d, 2H), 1.53-1.49 (t, 3H).

Example 3

1-Propylpyridinium Allylsulfonate

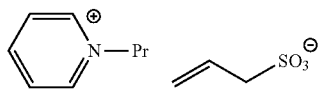

*Pr=propyl group

By the same operation except that instead of methyl allylsulfonate in Example 1, propyl allylsulfonate was used, 1-propylpyridinium allylsulfonate (28.2 g, 0.116 mol, 74% yield) was obtained. Melting point was 36° C. Measurement result of ¹H NMR was shown as follows:

¹H NMR (CD₃CN); δ=8.84-8.82 (d, 2H), 8.48-8.42 (t, 1H), 8.01-7.97 (d, 2H), 5.94-5.87 (m, 1H), 5.07-5.00 (m, 2H), 4.52-4.48 (t, 2H), 3.27-3.25 (d, 2H), 1.97-1.91 (m, 2H), 0.91-0.88 (t, 3H).

Example 4

1-Isopropylpyridinium Allylsulfonate

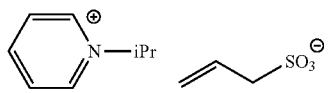

*iPr=isopropyl group

By the same operation except that instead of methyl allylsulfonate in Example 1, isopropyl allylsulfonate was used, 1-isopropylpyridinium allylsulfonate (22.9 g, 0.094 mol, 60% yield) was obtained. Melting point was 65° C. Measurement result of ¹H NMR was shown as follows:

¹H NMR (CD₃CN); δ=8.86-8.77 (d, 2H), 8.51-8.47 (t, 1H), 8.04-7.95 (d, 2H), 5.96-5.94 (m, 1H), 5.12-5.06 (m, 2H), 4.98-4.93 (t, 1H), 3.32-3.30 (t, 2H), 1.64-1.63 (t, 3H).

Example 5

1-Butylpyridinium Allylsulfonate

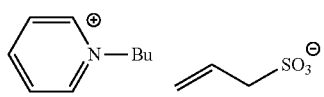

*Bu=butyl group

By the same operation except that instead of methyl allylsulfonate in Example 1, butyl allylsulfonate was used, 1-butylpyridinium allylsulfonate (39.7 g, 0.154 mol, 92% yield) was obtained. Melting point was 46° C. Measurement result of ¹H NMR was shown as follows:

¹H NMR (D₂O); δ=8.72-8.71 (d, 2H), 8.43-8.39 (t, 1H), 7.96-7.92 (d, 2H), 5.84-5.73 (m, 1H), 5.27-5.21 (m, 2H), 4.50-4.47 (q, 2H), 3.51-3.49 (q, 2H), 1.91-1.83 (m, 2H), 1.28-1.19 (m, 2H), 0.83-0.79 (t, 3H).

Example 6

1-Ethyl-4-methoxypyridinium Allylsulfonate

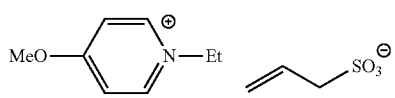

By the same operation except that instead of pyridine in Example 2, 4-methoxypyridine was used, 1-ethyl-4-methoxypyridinium allylsulfonate (34.6 g, 0.133 mol, 85% yield) was obtained. Melting point was −15° C. or less. Viscosity was 792 mPa·s. Measurement result of ¹H NMR was shown as follows:

¹H NMR (CD₃CN); δ=8.64-8.62 (d, 2H), 7.43-7.41 (d, 2H), 5.98-5.91 (m, 1H), 5.12-5.04 (m, 2H), 4.46-4.40 (q, 2H), 4.07 (s, 3H), 3.30-3.29 (d, 2H), 1.53-1.49 (t, 3H).

Example 7

1-Methylpyridinium 2-methylallylsulfonate

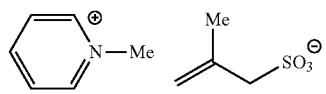

By the same operation except that instead of methyl allylsulfonate in Example 1, methyl 2-methylallylsulfonate was used, 1-methylpyridinium 2-methylallylsulfonate (24.2 g, 0.106 mol, 99% yield) was obtained. Melting point was 88° C. Measurement result of ¹H NMR was shown as follows:

¹H NMR (CD₃CN); δ=8.85-8.84 (d, 2H), 8.50-8.46 (t, 1H), 8.00-7.96 (d, 2H), 4.82-4.80 (m, 2H), 4.35 (s, 3H), 3.29-3.28 (d, 2H), 1.87 (s, 3H).

Example 8

1-Ethylpyridinium 2-methylallylsulfonate

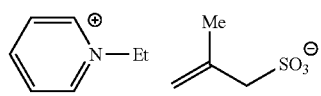

By the same operation except that instead of methyl allylsulfonate in Example 1, ethyl 2-methylallylsulfonate was used, 1-ethylpyridinium 2-methylallylsulfonate (33.2 g, 0.137 mol, 87% yield) was obtained. Melting point was 67° C. Measurement result of ¹H NMR was shown as follows:

$^1$H NMR (CD$_3$CN); δ=8.85-8.83 (d, 2H), 8.55-8.51 (t, 1H), 8.06-8.02 (d, 2H), 4.87-4.84 (m, 2H), 4.67-4.61 (d, 2H), 3.32 (s, 2H), 1.93-1.90 (s, 3H), 1.64-1.61 (t, 3H).

Example 9

1,3-Dimethylimidazolium Allylsulfonate

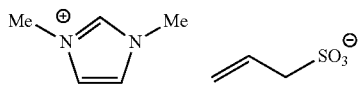

By the same operation except that instead of pyridine in Example 1, 1-methylimidazole was used, 1,3-dimethylimidazolium allylsulfonate (34.3 g, 0.157 mol, 100% yield) was obtained. Melting point was 30° C. Measurement result of $^1$H NMR was shown as follows:

$^1$H NMR (CD$_3$CN); δ=8.91 (s, 1H), 7.37 (s, 2H), 5.99-5.88 (m, 1H), 5.13-5.05 (m, 2H), 3.83 (s, 6H), 3.32-3.30 (d, 2H).

Example 10

1-Ethyl-3-methylimidazolium Allylsulfonate

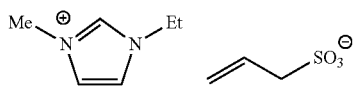

By the same operation except that instead of pyridine in Example 2, 1-methylimidazole was used, 1-ethyl-3-methylimidazolium allylsulfonate (35.5 g, 0.153 mol, 98% yield) was obtained. Melting point was −15° C. or less. Viscosity was 210 mPa·s. Measurement result of $^1$H NMR was shown as follows:

$^1$H NMR (D$_2$O); δ=8.55 (s, 1H), 7.33 (s, 1H), 7.27 (s, 1H), 5.84-5.73 (m, 1H), 5.27-5.22 (m, 2H), 4.10-4.05 (q, 2H), 3.52-3.50 (d, 2H), 1.37-1.33 (t, 3H).

Example 11

1-Propyl-3-methylimidazolium Allylsulfonate

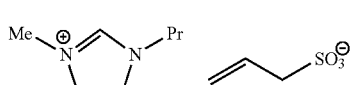

By the same operation except that instead of pyridine in Example 3, 1-methylimidazole was used, 1-propyl-3-methylimidazolium allylsulfonate (32.9 g, 0.133 mol, 85% yield) was obtained. Melting point was −15° C. or less. Viscosity was 419 mPa·s. Measurement result of $^1$H NMR was shown as follows:

$^1$H NMR (CD$_3$CN) ; δ=8.92 (s, 1H), 7.40-7.37 (d, 2H), 5.98-5.91 (m, 1H), 5.12-5.05 (m, 2H), 4.12-4.09 (t, 2H), 3.84 (s, 3H), 3.31-3.29 (d, 2H), 1.86-1.81 (m, 2H), 0.91-0.88 (t, 3H)

Example 12

1-Isopropyl-3-methylimidazolium Allylsulfonate

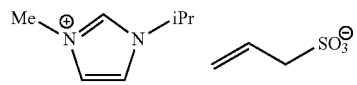

By the same operation except that instead of pyridine in Example 4, 1-methylimidazole was used, 1-isopropyl-3-methylimidazolium allylsulfonate (33.3 g, 0.135 mol, 86% yield) was obtained. Melting point was −15° C. or less. Viscosity was 728 mPa·s. Measurement result of $^1$H NMR was shown as follows:

$^1$H NMR (CD$_3$CN); δ=8.96 (s, 1H), 7.46 (s, 1H), 7.37 (s, 1H), 5.96-5.93 (m, 1H), 5.12-5.05 (m, 2H), 4.62-4.57 (m, 1H), 3.84 (s, 3H), 3.32-3.30 (d, 2H), 1.50-1.48 (s, 6H).

Example 13

1-Butyl-3-methylimidazolium Allylsulfonate

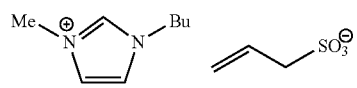

By the same operation except that instead of pyridine in Example 5, 1-methylimidazole was used, 1-butyl-3-methylimidazolium allylsulfonate (40.9 g, 0.157 mol, 100%) yield) was obtained. Melting point was −15° C. or less. Viscosity was 451 mPa·s. Measurement result of $^1$H NMR was shown as follows:

$^1$H NMR (D$_2$O); δ=8.56 (s, 1H), 7.33 (s, 1H), 7.28 (s, 1H), 5.82-5.75 (m, 1H), 5.26-5.21 (m, 2H), 4.07-4.03 (t, 2H), 3.75 (s, 3H), 3.51-3.49 (d, 2H), 1.74-1.67 (m, 2H), 1.22-1.13 (m, 2H), 0.80-0.76 (t, 3H).

Example 14

1-Allyl-3-methylimidazolium Allylsulfonate

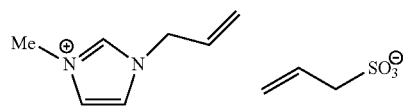

By the same operation except that instead of pyridine in Example 1, 1-allylimidazole was used, 1-allyl-3-methylimidazolium allylsulfonate (35.3 g, 0.144 mol, 92% yield) was obtained. Melting point was −15° C. or less. Viscosity was 236 mPa·s. Measurement result of $^1$H NMR was shown as follows:

$^1$H NMR (CD$_3$CN); δ=8.94 (s, 1H), 7.39-7.37 (d, 2H), 6.05-5.90 (m, 2H), 5.39-5.33 (t, 2H), 5.12-5.05 (t, 2H), 4.79-4.78 (d, 2H), 3.85 (s, 3H), 3.31-3.29 (d, 2H).

Example 15

1-Allyl-3-ethylimidazolium Allylsulfonate

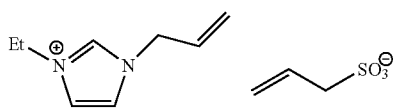

By the same operation except that instead of pyridine in Example 2, 1-allylimidazole was used, 1-allyl-3-ethylimidazolium allylsulfonate (36.5 g, 0.141 mol, 90% yield) was obtained. Melting point was −15° C. or less. Viscosity was 205 mPa·s. Measurement result of $^1$H NMR was shown as follows:

$^1$H NMR (CD$_3$CN); δ=9.01 (s, 1H), 7.46-7.39 (d, 2H), 6.04-5.93 (m, 2H), 5.38-5.34 (t, 2H), 5.12-5.05 (t, 2H), 4.80-4.79 (d, 2H), 4.21-4.19 (d, 2H), 3.31-3.29 (d, 2H), 1.48-1.44 (s, 3H).

Example 16

1-Allyl-3-butylimidazolium Allylsulfonate

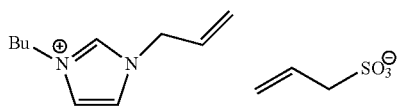

By the same operation except that instead of pyridine in Example 5, 1-allylimidazole was used, 1-allyl-3-butylimidazolium allylsulfonate(30.6 g, 0.107 mol, 68% yield) was obtained. Melting point was −15° C. or less. Viscosity was 270 mPa·s. Measurement result of $^1$H NMR was shown as follows:

$^1$H NMR (CD$_3$CN); δ=8.90 (s, 1H), 7.42-7.38 (d, 2H), 6.04-5.91 (m, 2H), 5.40-5.33 (t, 2H), 5.12-5.05 (t, 2H), 4.79-4.77 (d, 2H), 4.17-4.13 (d, 2H), 3.30-3.28 (d, 2H), 1.83-1.79 (q, 2H), 1.34-1.29 (q, 2H), 0.95-0.91 (s, 3H).

Example 17

1,3-Dimethylimidazolium 2-methylallylsulfonate

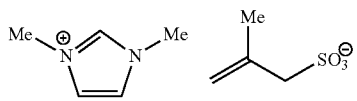

By the same operation as except that instead of methyl allylsulfonate in Example 9, methyl 2-methylallylsulfonate was used, 1,3-dimethylimidazolium 2-methylallylsulfonate (16.0 g, 0.069 mol, 44% yield) was obtained. Melting point was 119° C. Measurement result of $^1$H NMR was shown as follows:

$^1$H NMR (CD$_3$CN); δ=8.77 (s, 1H), 7.36 (s, 2H), 4.87-4.84 (d, 2H), 3.86 (s, 6H), 3.33 (s, 2H), 1.93-1.89 (d, 3H).

Example 18

1-Ethyl-3-methylimidazolium 2-methylallylsulfonate

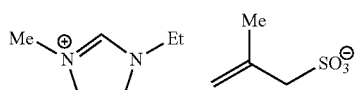

By the same operation except that instead of ethyl allylsulfonate in Example 10, ethyl 2-methylallylsulfonate was used, 1-ethyl-3-methylimidazolium 2-methylallylsulfonate(33.3 g, 0.135 mol, 86% yield) was obtained. Melting point was 52° C. Measurement result of $^1$H NMR was shown as follows:

$^1$H NMR (CD$_3$CN); δ=9.07 (s, 1H), 7.48-7.42 (d, 2H), 4.88-4.88(d, 2H), 4.26-4.21 (q, 2H), 3.89 (s, 3H), 3.35 (s, 2H), 1.93 (s, 3H), 1.51-1.47 (t, 3H).

Example 19

1-Ethyl-2,3-dimethylimidazolium Allylsulfonate

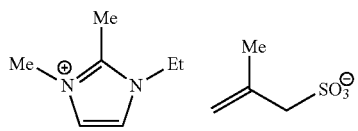

By the same operation except that instead of pyridine in Example 2, 1,2-dimethylimidazole was used, 1-ethyl-2,3-dimethylimidazolium allylsulfonate (37.1 g, 0.151 mol, 96% yield) was obtained. Melting point was 82° C. Measurement result of $^1$H NMR was shown as follows:

$^1$H NMR (CD$_3$CN); δ=7.27-7.24 (d, 2H), 5.98-5.89 (m, 1H), 5.10-5.04 (m, 2H), 4.07-4.05 (d, 2H), 3.68 (s, 3H), 3.27-3.25 (d, 2H), 2.48 (s, 3H), 1.39-1.35 (s, 3H).

Example 20

1-Butyl-2,3-dimethylimidazolium Allylsulfonate

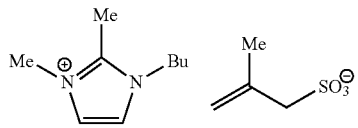

By the same operation except that instead of pyridine in Example 5, 1,2-dimethylimidazole was used, 1-butyl-2,3-dimethylimidazolium allylsulfonate (34.0 g, 0.124 mol, 79% yield) was obtained. Melting point was 63° C. Measurement result of $^1$H NMR was shown as follows:

$^1$H NMR (CD$_3$CN); δ=7.26 (s, 2H), 5.95-5.91 (m, 1H), 5.10-5.04 (m, 2H), 4.04-4.00 (t, 2H), 3.68 (s, 3H), 3.27-3.25 (d, 2H), 2.48 (s, 3H), 1.74-1.70 (m, 2H), 1.36-1.30 (m, 2H), 0.95-0.91 (t, 3H).

Example 21

Triethylmethylammonium Allylsulfonate

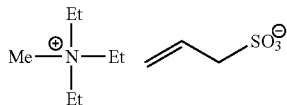

By the same operation except that instead of pyridine in Example 1, triethylamine was used, triethylmethylammonium allylsulfonate (29.8 g, 0.126 mol, 80% yield) was obtained. Melting point was 43° C. Measurement result of $^1$H NMR was shown as follows:

$^1$H NMR (CD$_3$CN); δ=5.98-5.91 (m, 1H), 5.10-5.05 (m, 2H), 3.28-3.30 (m, 8H), 2.84 (s, 3H), 1.24-1.22 (t, 9H).

Example 22

Ethyltrimethylammonium Allylsulfonate

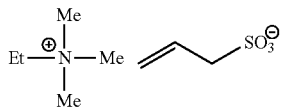

By the same operation except that instead of pyridine in Example 1, ethyldimethylamine was used, ethyltrimethylammonium allylsulfonate (19.7 g, 0.094 mol, 60% yield) was obtained. Melting point was 110° C. Measurement result of $^1$H NMR was shown as follows:

$^1$H NMR (CD$_3$CN); δ=5.95-5.93 (m, 1H), 5.11-5.05 (m, 2H), 3.34-3.27 (m, 4H), 3.00 (s, 9H), 1.30-1.28 (t, 3H).

Example 23

Hexyltrimethylammonium Allylsulfonate

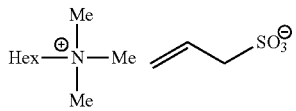

*Hex=hexyl group

In the solvent of acetonitrile, hexyltrimethylammonium bromide (35.2 g, 0.157 mol) and silver allylsulfonate (35.9 g, 0.157 mol, 1 eq) were reacted under reflux by heating for 6 hours. After completed the reaction, precipitated silver bromide was filtered off, pale brown oil was obtained by vacuum concentration. After adsorptive treatment by activated carbon, activated carbon was filtered off, then, the desired product of hexyltrimethylammonium allylsulfonate (15.8 g, 0.060 mmol, 38% yield) was obtained by vacuum concentration. Melting point was 150° C. Measurement result of $^1$H NMR was shown as follows:

$^1$H NMR (CD$_3$CN); δ=5.95-5.93 (m, 1H), 5.11-5.05 (m, 2H), 3.28-3.18 (m, 4H), 3.00 (s, 9H), 1.69-1.66 (m, 2H), 1.32-1.30 (m, 6H), 0.91-0.89 (t, 3H).

Example 24

Octyltrimethylammonium Allylsulfonate

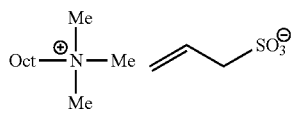

*Oct=octyl group

By the same operation except that instead of hexyltrimethylammonium bromide in Example 23, octyltrimethylammonium bromide was used, octyltrimethylammonium allylsulfonate (34.6 g, 0.118 mol, 75% yield) was obtained. Melting point was 165° C. Measurement result of $^1$H NMR was shown as follows:

$^1$H NMR (CD$_3$CN); δ=5.96-5.94 (m, 1H), 5.11-5.05 (m, 2H), 3.28-3.26 (d, 2H), 3.21-3.17 (m, 2H), 3.00 (s, 9H), 1.69-1.66 (m, 2H), 1.32-1.30 (m, 10H), 0.89-0.87 (t, 3H).

Example 25

1,1-Dimethylpyrrolidinium Allylsulfonate

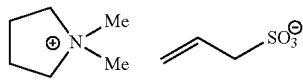

By the same operation except that instead of pyridine in Example 1, 1-methylpyrrolidine was used, 1,1-dimethylpyrrolidinium allylsulfonate (30.2 g, 0.137 mol, 87% yield) was obtained. Melting point was 73° C. Measurement result of $^1$H NMR was shown as follows:

$^1$H NMR (CD$_3$CN); δ=5.96-5.91 (m, 1H), 5.11-5.05 (m, 2H), 3.45-3.43 (m, 4H), 3.28-3.26 (d, 2H), 3.06 (s, 6H), 2.17-2.14 (m, 4H).

Example 26

1,1-Dimethylpiperidinium Allylsulfonate

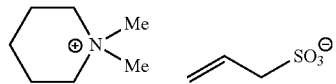

By the same operation except that instead of pyridine in Example 1, 1-methylpiperidine was used, 1,1-dimethylpiperidinium allylsulfonate (35.5 g, 0.151 mol, 96% yield) was obtained. Melting point was 98° C. Measurement result of $^1$H NMR was shown as follows:

$^1$H NMR (CD$_3$CN); δ=5.97-5.93 (m, 1H), 5.11-5.05 (m, 2H), 3.28-3.26 (d, 6H), 3.02 (s, 6H), 1.82-1.80 (m, 4H), 1.63-1.57 (m, 2H).

Example 27

1-ethyl-1-methylpyrrolidinium allylsulfonate

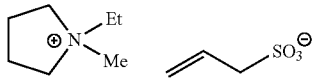

By the same operation except that instead of pyridine in Example 1, 1-ethylpyrrolidine was used, 1-ethyl-3-methylpyrrolidinium allylsulfonate (32.2 g, 0.137 mol, 87% yield) was obtained. Melting point was <−15° C. Viscosity was 312 mPa·s. Measurement result of $^1$H NMR was shown as follows:

$^1$H NMR (CD$_3$CN); δ=5.95-5.91 (m, 1H), 5.11-5.05 (m, 2H), 3.41-3.26 (m, 8H), 2.93 (s, 3H), 2.15-2.12 (m, 4H), 1.31-1.30 (t, 3H).

Example 28

1-Ethyl-1-methylpiperidinium Allylsulfonate

By the same operation except that instead of pyridine in Example 1, 1-ethylpiperidine was used, 1-ethyl-1-methylpiperidinium allylsulfonate (23.9 g, 0.096 mol, 61% yield) was obtained. Melting point was 50° C. Measurement result of $^1$H NMR was shown as follows:

$^1$H NMR (CD$_3$CN); δ=5.98-5.91 (m, 1H), 5.11-5.05 (m, 2H), 3.34-3.22 (m, 8H), 2.91 (s, 3H), 1.81-1.79 (m, 4H), 1.63-1.60 (m, 2H), 1.27-1.25 (t, 3H).

Example 29

1-Butyl-1-methylpyrrolidinium Allylsulfonate

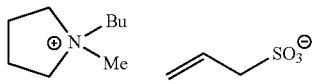

By the same operation except that instead of hexyltrimethylammonium bromide in Example 23, 1-butyl-1-methylpyrrolidinium bromide was used, 1-butyl-1-methylpyrrolidinium allylsulfonate (34.3 g, 0.130 mol, 83% yield) was obtained. Melting point was 39° C. Measurement result of $^1$H NMR was shown as follows:

$^1$H NMR (CD$_3$CN); δ=5.97-5.91 (m, 1H), 5.11-5.05 (m, 2H), 3.42-3.40 (m, 4H), 3.28-3.23 (m, 4H), 2.95 (s, 3H), 2.13-2.11 (m, 4H), 1.73-1.68 (m, 2H), 1.39-1.33 (m, 2H), 0.97-0.93 (t, 3H).

Example 30

1-Butyl-1-methylpiperidinium Allylsulfonate

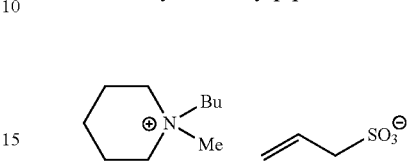

By the same operation except that instead of hexyltrimethylammonium bromide in Example 23, 1-butyl-1-methylpiperidinium bromide was used, 1-butyl-1-methylpiperidinium allylsulfonate (40.5 g, 0.146 mol, 93% yield) was obtained. Melting point was 48° C. Measurement result of $^1$H NMR was shown as follows:

$^1$H NMR (CD$_3$CN); δ=5.95-5.91 (m, 1H), 5.11-5.05 (m, 2H), 3.29-3.22 (m, 8H), 2.92 (s, 3H), 1.80-1.78 (m, 4H), 1.65-1.61 (m, 4H), 1.36-1.33 (m, 2H), 0.97-0.93 (t, 3H).

Example 31

N,N-dimethylmorpholinium Allylsulfonate

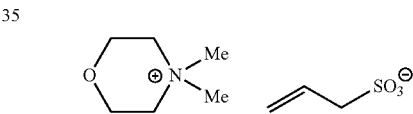

By the same operation except that instead of pyridine in Example 1, N-methylmorpholine was used, N,N-dimethylmorpholinium allylsulfonate (24.2 g, 0.102 mol, 65% yield) was obtained. Melting point was <−15° C. Measurement result of $^1$H NMR was shown as follows:

$^1$H NMR (CD$_3$CN); δ=5.97-5.90 (m, 1H), 5.12-5.07 (m, 2H), 3.90-3.88 (d, 4H), 3.42-3.40 (d, 4H), 3.30-3.28 (d, 2H), 3.19 (s, 6H).

Example 32

N-Ethyl-N-methylmorpholinium Allylsulfonate

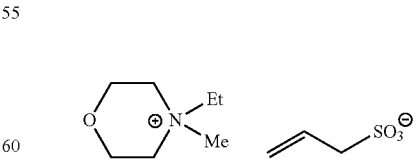

By the same operation except that instead of pyridine in Example 1, N-ethylmorpholine was used, N-ethyl-N-methylmorpholinium allylsulfonate (26.4 g, 0.105 mol, 67% yield) was obtained. Melting point was <−15° C. Measurement result of $^1$H NMR was shown as follows:

¹H NMR (CD₃CN); δ=5.97-5.90 (m, 1H), 5.11-5.06 (m, 2H), 3.91-3.89 (d, 4H), 3.52-3.46 (q, 2H), 3.37-3.35 (m, 4H), 3.29-3.27 (d, 2H), 3.08 (s, 3H), 1.32-1.28 (t, 3H).

Example 33

1-(Hydroxyethyl)-1-methylpiperidinium Allylsulfonate

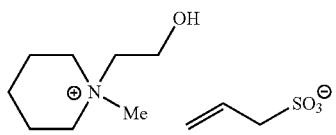

By the same operation except that instead of pyridine in Example 1, 1-(hydroxyethyl)piperidine was used, 1-(hydroxyethyl)-1-methylpiperidinium allylsulfonate (35.0 g, 0.132 mol, 84% yield) was obtained. Melting point was <−15° C. Viscosity was 2353 mPa·s. Measurement result of ¹H NMR was shown as follows:

¹H NMR (CD₃CN); δ=5.97-5.90 (m, 1H), 5.15-5.09 (m, 2H), 4.93-4.90 (t, 1H), 3.94-3.91 (m, 2H), 3.48-3.44 (m, 4H), 3.34-3.32 (m, 4H), 3.08 (s, 3H), 1.84-1.81 (m, 4H), 1.62-1.59 (t, 3H).

Comparative Example 1

1-Methylpyridinium Methanesulfonate

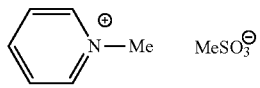

By the same operation except that instead of methyl allylsulfonate in Example 1, methyl methanesulfonate was used, 1-methylpyridinium methanesulfonate (24.6 g, 0.130 mol, 83% yield) was obtained. Melting point was 135° C. Measurement result of ¹H NMR was shown as follows:

¹H NMR (D₂O); δ=8.68-8.66 (d, 2H), 8.44-8.40 (t, 1H), 7.95-7.92 (t, 2H), 4.28 (s, 3H), 2.69 (s, 3H).

Comparative Example 2

1-Butylpyridinium Methanesulfonate

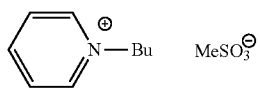

By the same operation except that instead of butyl allylsulfonate in Example 5, butyl methanesulfonate was used, 1-butylpyridinium methanesulfonate (23.2 g, 0.100 mol, 64% yield) was obtained. Melting point was 73° C. Measurement result of ¹H NMR was shown as follows:

¹H NMR (CD₃OD); δ=9.00-8.99 (d, 2H), 8.62-8.58 (t, 1H), 8.13-8.12 (t, 2H), 4.65-4.57 (t, 2H), 2.69 (s, 3H), 2.04-1.96 (m, 2H), 1.46-1.37 (m, 2H), 1.03-0.99 (t, 3H).

Comparative Example 3

1-Ethyl-4-methoxypyridinium methanesulfonate

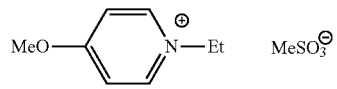

By the same operation except that instead of ethyl allylsulfonate in Example 6, ethyl methanesulfonate was used, 1-ethyl-4-methoxypyridinium methanesulfonate (22.3 g, 0.096 mol, 61% yield) was obtained. Melting point was 84° C. Measurement result of ¹H NMR was shown as follows:

¹H NMR (CD₃CN); δ=8.51-8.49 (d, 2H), 7.39-7.37 (d, 2H), 4.41-4.36 (q, 2H), 4.07 (s, 3H), 2.41 (s, 3H), 1.53-1.49 (t, 3H).

Comparative Example 4

1-Butylpyridinium Trifluoromethanesulfonate

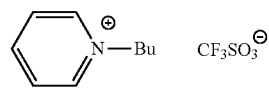

By the same operation except that instead of butyl allylsulfonate in Example 5, butyl trifluoromethanesulfonate was used, 1-butylpyridinium trifluoromethanesulfonate (44.8 g, 0.157 mol, 100% yield) was obtained. Melting point was 32° C. Measurement result of ¹H NMR was shown as follows:

¹H NMR (CD₃CN); δ=8.73-8.70 (d, 2H), 8.50-8.47 (t, 1H), 8.09-8.05 (t, 2H), 4.55-4.50 (t, 2H), 1.94-1.92 (m, 2H), 1.39-1.34 (m, 2H), 0.94-0.91 (t, 3H).

Comparative Example 5

1,3-Dimethylimidazolium Methanesulfonate

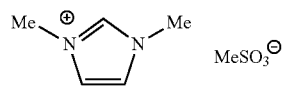

By the same operation except that instead of methyl allylsulfonate in Example 9, methyl methanesulfonate was used, 1,3-dimethylimidazolium methanesulfonate (13.6 g, 0.071 mol, 45% yield) was obtained. Melting point was 76° C. Measurement result of ¹H NMR was shown as follows:

¹H NMR (D₂O); δ=8.49 (s, 1H), 7.26 (s, 2H), 3.73 (s, 6H), 2.65 (s, 3H).

Comparative Example 6

1-Ethyl-3-methylimidazolium Methanesulfonate

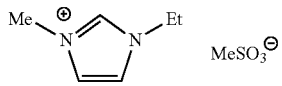

By the same operation except that instead of ethyl allylsulfonate in Example 10, ethyl methanesulfonate was used, 1-ethyl-3-methylimidazolium methanesulfonate (28.8 g, 0.124 mol, 79% yield) was obtained. Melting point was 38° C. Measurement result of $^1$H NMR was shown as follows:

$^1$H NMR (D$_2$O); δ=9.24 (s, 1H), 7.55-7.49 (d, 2H), 4.22-4.17 (q, 2H), 3.85 (s, 3H), 2.45 (s, 3H), 1.43-1.40 (t, 3H).

Comparative Example 7

1-Butyl-3-dimethylimidazolium Methanesulfonate

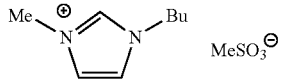

By the same operation except that instead of ethyl allylsulfonate in Example 10, ethyl methanesulfonate was used, 1-butyl-3-dimethylimidazolium methanesulfonate (28.8 g, 0.124 mol, 79% yield) was obtained. Melting point was 77° C. Measurement result of $^1$H NMR was shown as follows:

$^1$H NMR (CDCl$_3$); δ=9.65 (s, 1H), 7.47-7.36 (d, 2H), 4.12-4.10 (t, 2H), 3.89 (s, 3H), 2.59 (s, 3H), 1.72 (q, 2H), 1.21-1.98 (m, 2H), 0.80-0.78 (t, 3H).

As apparent from the result of Example 1 to 7, the ionic liquid of the present invention represented by the general formula [1] (particularly the one represented by the general formula [3]) was found to be liquid at 100° C. or less.

In addition, as apparent from the result of Comparative Example 1, the conventional ionic liquid having methanesulfonate as anion, and 1-methylpyridinium ion as cation was found not to become liquid at 100° C. or less.

Further, as apparent from the result of the Comparative Example 3, the conventional halogenic ionic liquid having trifluoromethanesulfonate as anion becomes liquid at 100° C. or less, but has the problem that exhibits corrosive property due to the halogen-containing compound.

Furthermore, as apparent from the result of the comparison of Example 1 and Comparative Example 1, the comparison of Example 5 and Comparative Example 2, the comparison of Example 9 and Comparative Example 5, Example 10 and Comparative Example 6, and Example 13 and Comparative Example 7, when cation is 1-methylpyridinium ion, 1-butylpyridinium ion, 1,3-dimethylimidazolium ion, 1-ethyl-3-methylimidazolium ion and 1-butyl-3-methylimidazolium ion, compared with the conventional ionic liquid using methanesulfonate as anion, the ionic liquid of the present invention, that is, the ionic liquid having allylsulfonate as anion was found to more decrease the melting point.

Example 34

Methylenebispyridinium Allylsulfonate

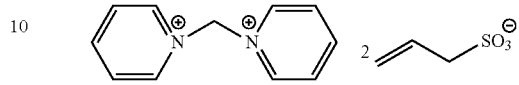

Methylenebisallylsulfonate (1.0 g, 0.004 mol) synthesized according to the usual method (for example, WO2008/032463 and the like) and pyridine (0.62 g, 0.008 mol, 2.0 eq) were reacted by stirring at 40° C. for 2 hours. After completed the reaction, unreacted pyridine was distilled off under reduced pressure, and reaction product was completely dissolved in methanol. After dissolution, acetone was added, and cooled to recrystallize. Crystal was dried by heating under reduced pressure to obtain the desired product of methylenebispyridinium allylsulfonate (0.96 g, 0.002 mol, 59% yield). Melting point was 174° C. Measurement result of $^1$H NMR was as follows:

$^1$H NMR (CD$_3$OD); δ=9.42-9.41 (d, 4H), 8.86-8.82 (t, 2H), 8.33-8,30 (t, 4H), 7.38 (s, 2H), 6.02-5.91 (m, 2H), 5.29-5.21 (dd, 4H), 3.54-3.51 (d, 4H).

Example 35

Methylenebis(1-methylimidazolium) Allylsulfonate

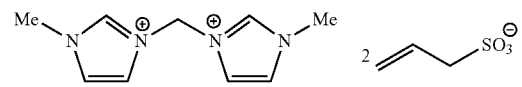

By the same operation except that instead of pyridine in Example 34, 1-methylimidazole was used, methylenebis(1-methylimidazolium) allylsulfonate (1.16 g, 0.003 mol, 70% yield) was obtained. Melting point was 110° C. Measurement result of $^1$H NMR was shown as follows:

$^1$H NMR (CD$_3$OD); δ=8.15 (s, 2H), 7.92 (s, 2H), 7.69 (s, 2H), 6.69 (s, 2H), 6.02-5.92 (m, 2H), 5.30-5.21 (dd, 4H), 3.98 (s, 6H), 3.55-3.52 (d, 4H).

Example 36

Methylenebispyridinium 2-methylallylsulfonate

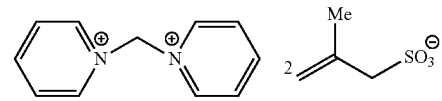

By the same operation except that instead of methylenebisallylsulfonate in Example 34, methylenebis(2-methylallylsulfonate) was used, methylenebispyridinium 2-methylallylsulfonate (0.85 g, 0.002 mol, 68% yield) was obtained. Melting point was 165° C. Measurement result of $^1$H NMR was shown as follows:

$^1$H NMR (CD$_3$OD); δ=9.43-9.42 (d, 4H), 8.86-8.83 (t, 2H), 8.34-8.30 (t, 4H), 7.39 (s, 2H), 4.98-4.97 (d, 4H), 3.52 (s, 4H), 1.93 (s, 6H).

Comparative Example 8

Methylenebispyridinium Methanesulfonate

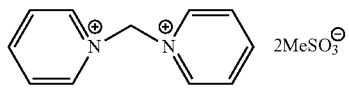 [SMILES: c1cc[n+](C[n+]2ccccc2)cc1]

By the same operation except that instead of methylenebisallylsulfonate in Example 34, methylenebismethanesulfonate was used, methylenebispyridinium methanesulfonate (1.5 g, 0.004 mol, 82% yield) was obtained. Melting point was 223° C. Measurement result of $^1$H NMR was shown as follows:

$^1$H NMR (CD$_3$OD); δ=9.44-9.43 (d, 4H), 8.86-8.81 (t, 2H), 8.34-8.30 (m, 4H), 7.39 (s, 2H).

As apparent from the result of Examples 34 to 36, the ionic liquid of the present invention represented by the general formula [1] (particularly the one represented by the general formula [4]) was found to exhibit liquid at 200° C. or less.

In addition, as apparent from the result of the comparison between Example 34 and Comparative Example 8, when cation is methylenebispyridinium ion, compared with the conventional ionic liquid using methanesulfonate as anion, the ionic liquid of the present invention, that is, the ionic liquid having allylsulfonate as anion was found to more decrease the melting point.

Example 37

Pyridinium Allylsulfonate

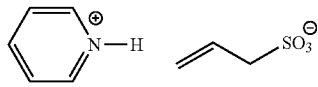

Allysulfonic acid (2.0 g, 0.014 mol) synthesized by salt exchange according to cation exchanging resin and pyridine (1.7 g, 0.022 mol, 1.5 eq) were reacted by stirring at room temperature for 2 hours. After completed the reaction, unreacted pyridine was distilled off under the reduced pressure, reaction product was completely dissolved in acetonitrile. After dissolution, ethyl acetate was added, and cooled to recrystallize. Crystal was dried by heating under the reduced pressure to obtain the desired product of pyridinium allylsulfonate (2.0 g, 0.010 mol, 64% yield). Melting point was 97° C. Measurement result of $^1$H NMR was shown as follows:

$^1$H NMR (CD$_3$CN); δ=8.78-8.76 (d, 2H), 8.50-8.46 (t, 1H), 7.97-7.94 (t, 2H), 6.01-5.94 (m, 1H), 5.23-5.13 (m, 2H), 3.51-3.49 (t, 2H).

Example 38

1-Methylimidazolium Allylsulfonate

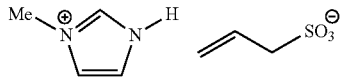

By the same operation except that instead of pyridine in Example 37, 1-methylimidazole was used, 1-methylimidazolium allylsulfonate (2.2 g, 0.011 mol, 77% yield) was obtained. Melting point was 52° C. Measurement result of $^1$H NMR was shown as follows:

$^1$H NMR (CD$_3$CN); δ=8.11 (s, 1H), 7.20-7.18 (d, 2H), 5.99-5.92 (m, 1H), 5.19-5.11 (m, 2H), 3.76 (s, 3H), 3.43-3.42 (d, 2H).

Comparative Example 9

Pyridinium Methanesulfonate

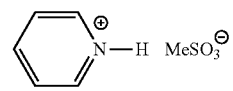

By the same operation except that instead of allylsulfonic acid in Example 37, methanesulfonic acid was used, pyridinium methanesulfonate (2.3 g, 0.013 mol, 92% yield) was obtained. Melting point was 189° C. Measurement result of $^1$H NMR was shown as follows:

$^1$H NMR (CD$_3$CN); δ=8.80-8.79 (d, 2H), 8.52-8.48 (t, 1H), 7.99-7.95 (t, 2H), 2.65 (s, 3H)

Comparative Example 10

1-Methylimidazolium Methanesulfonate

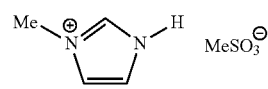

By the same operation except that instead of allylsulfonic acid in Example 38, methanesulfonic acid was used, 1-methylimidazolium methanesulfonate (2.3 g, 0.013 mol, 93% yield) was obtained. Melting point was 133° C. Measurement result of $^1$H NMR was shown as follows:

$^1$H NMR (CD$_3$CN); δ=8.36 (s, 1H), 7.24-7.15 (d, 2H), 3.67 (s, 3H), 2.42 (s, 3H).

Example 39

Tributylmethylphosphonium Allylsulfonate

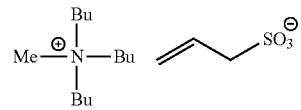

By the same operation except that instead of pyridine in Example 1, tributylphosphine was used, tributylmethylphosphonium allylsulfonate (50.0 g, 0.148 mol, 94% yield) was obtained. Melting point was 45° C. Measurement result of $^1$H NMR was shown as follows:

$^1$H NMR (CD$_3$CN); δ=5.95-5.93 (m, 1H), 5.11-5.05 (m, 2H), 3.28-3.26 (d, 2H), 2.06-2.01 (m, 6H), 1.70-1.67 (d, 3H), 1.47-1.44 (m, 12H), 0.95-0.92 (t, 9H).

The invention claimed is:
1. An ionic liquid of formula [1]:

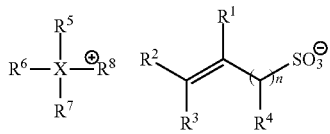
[1]

wherein
- $R^1$ to $R^3$ and n number of $R^4$ are each independently a hydrogen atom or an alkyl group having 1 to 4 carbon atoms,
- $R^5$ to $R^7$ are each independently an alkyl group optionally substituted with a hydroxyl group or an alkoxy group, an aralkyl group, or an aryl group,
- $R^8$ is an alkyl group optionally substituted with a hydroxy group or an alkoxy group, an aralkyl group, an aryl group, or a group of formula [2]:

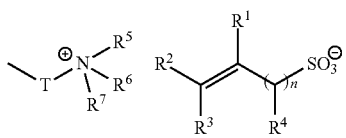
[2]

wherein
- T is an alkylene chain having 1 to 8 carbon atoms,
- n is 1 or 2, and
- $R^1$ to $R^7$ are the same as above,
- X is a nitrogen atom or a phosphorus atom,
- n is 1 or 2, and
- when n is 1, $R^3$ and $R^4$ may be bound together with the adjacent carbon atoms to form a cyclohexene ring,
- when X is a nitrogen atom, $R^5$ to $R^7$ or $R^5$ to $R^6$ may form a hetero ring with the nitrogen atom binding thereto, and
- when $R^8$ is a group of formula [2], X is a nitrogen atom.

2. The ionic liquid according to claim 1, wherein the ionic liquid is of formula [3]:

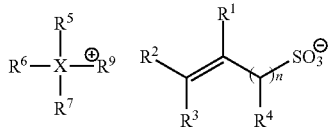
[3]

wherein
- $R^9$ is an alkyl group optionally substituted with a hydroxy group or an alkoxy group, an aralkyl group or an aryl group, and
- $R^1$ to $R^7$, X and n are the same as above, or the ionic liquid is of formula [4]:

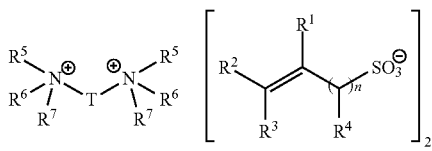
[4]

wherein $R^1$ to $R^7$, T and n are the same as above.

3. The ionic liquid according to claim 2, wherein the anion in formula [3] or [4] is allylsulfonate or 2-methylallylsulfonate.

4. The ionic liquid according to claim 2, wherein the cation in formula [3] is of one of formula [5] to [8] and [10] to [12]:

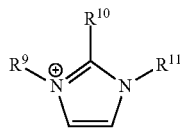
[5]

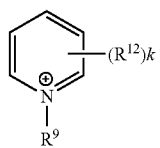
[6]

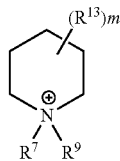
[7]

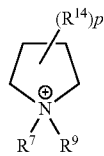
[8]

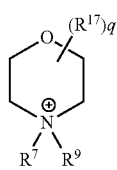
[10]

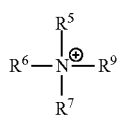
[11]

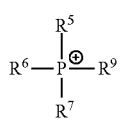
[12]

wherein
- $R^{10}$ to $R^{11}$ and $R^{15}$ to $R^{17}$ are each independently a hydrogen atom, an alkyl group, or an aralkyl group,
- $R^{12}$ to $R^{14}$ are each independently a hydrogen atom, an alkyl group, an aralkyl group, or an alkoxy group,
- k is an integer of 0 to 5,
- m is an integer of 0 to 10,
- p and q are integers of 0 to 8, and
- $R^5$ to $R^7$ and $R^9$ are the same as above.

5. The ionic liquid according to claim 2, wherein the cation in formula [4] is of formula [13] or formula [14]:

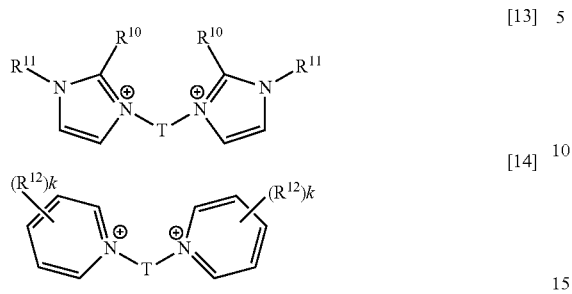

wherein $R^{10}$ to $R^{12}$, T, and k are the same as above.

6. The ionic liquid according to claim 1, wherein the ionic liquid of formula [1] is 1-ethyl-4-methoxypyridinium allylsulfonate, 1-ethyl-3-methylimidazolium allylsulfonate, 1-propyl-3-methylimidazolium allylsulfonate, 1-isopropyl-3-methylimidazolium allylsulfonate, 1-butyl-3-methylimidazolium allylsulfonate, 1-allyl-3-methylimidazolium allylsulfonate, 1-allyl-3-ethylimidazolium allylsulfonate, 1-allyl-3-butylimidazolium allylsulfonate, 1-ethyl-1-methylpyrrolidinium allylsulfonate, or 1-(hydroxyethyl)-1-methylpiperidinium allylsulfonate.

* * * * *